United States Patent
Jin et al.

(10) Patent No.: US 10,312,124 B2
(45) Date of Patent: Jun. 4, 2019

(54) SINGLE ULTRA-PLANAR WAFER TABLE STRUCTURE FOR BOTH WAFERS AND FILM FRAMES

(71) Applicant: SEMICONDUCTOR TECHNOLOGIES & INSTRUMENTS PTE LTD, Singapore (SG)

(72) Inventors: Jian Ping Jin, Singapore (SG); Leng Kheam Lee, Singapore (SG)

(73) Assignee: SEMICONDUCTOR TECHNOLOGIES & INSTRUMENTS PTE LTD, Singapore (SG)

(*) Notice: Subject to any disclaimer, the term of this patent is extended or adjusted under 35 U.S.C. 154(b) by 681 days.

(21) Appl. No.: 14/424,275

(22) PCT Filed: Sep. 2, 2013

(86) PCT No.: PCT/SG2013/000381
§ 371 (c)(1),
(2) Date: Feb. 26, 2015

(87) PCT Pub. No.: WO2014/035346
PCT Pub. Date: Mar. 6, 2014

(65) Prior Publication Data
US 2015/0214090 A1    Jul. 30, 2015

Related U.S. Application Data

(60) Provisional application No. 61/696,051, filed on Aug. 31, 2012.

(51) Int. Cl.
*B25B 27/14*    (2006.01)
*H01L 21/68*    (2006.01)
(Continued)

(52) U.S. Cl.
CPC ......... *H01L 21/681* (2013.01); *B25J 11/0095* (2013.01); *B25J 15/0616* (2013.01);
(Continued)

(58) Field of Classification Search
CPC ............. H01L 21/681; H01L 21/67144; H01L 21/68757; H01L 21/67706; H01L 21/6838;
(Continued)

(56) References Cited

U.S. PATENT DOCUMENTS 3,078,549 A * 2/1963 Wende ................. B28D 5/0058
29/418
5,421,595 A * 6/1995 Cripe .................... B25B 11/007
204/298.15
(Continued)

FOREIGN PATENT DOCUMENTS

CN    1938122 A    3/2007
JP    S62-8636 U    1/1987
(Continued)

OTHER PUBLICATIONS

International Search Report dated Nov. 21, 2013 on related Application No. PCT/SG2013/000381 filed Sep. 2, 2013.

*Primary Examiner* — David P Bryant
*Assistant Examiner* — Nirvana Deonauth
(74) *Attorney, Agent, or Firm* — Horizon IP Pte Ltd.

(57) ABSTRACT

A wafer table structure providing a single wafer table surface suitable for handling both wafers and film frames includes a base tray having a set of compartments formed therein by way of a set of ridges formed in or on an interior base tray surface; a hardenable fluid permeable compartment material disposed within the set of base tray compartments; and a set of openings formed in the base tray interior surface by which the hardened compartment material is exposable to
(Continued)

negative or positive pressures. The base tray includes a first ceramic material (e.g., porcelain), and the hardenable compartment material includes a second ceramic material. The base tray and the compartment material are simultaneously machinable by way of a standard machining process to thereby planarize exposed outer surfaces of the base tray and the hardened compartment material at an essentially identical rate for forming a highly or ultra-planar wafer table surface.

16 Claims, 16 Drawing Sheets

(51) Int. Cl.
*H01L 21/683* (2006.01)
*B25J 11/00* (2006.01)
*B25J 15/06* (2006.01)
*H01L 21/677* (2006.01)
*G01B 11/27* (2006.01)
*G01N 21/95* (2006.01)
*H01L 21/687* (2006.01)
*H01L 21/67* (2006.01)

(52) U.S. Cl.
CPC ....... *B25J 15/0658* (2013.01); *B25J 15/0666* (2013.01); *G01B 11/27* (2013.01); *G01N 21/9501* (2013.01); *H01L 21/67144* (2013.01); *H01L 21/67706* (2013.01); *H01L 21/6838* (2013.01); *H01L 21/68757* (2013.01); *G01N 2201/025* (2013.01); *Y10T 29/49826* (2015.01)

(58) Field of Classification Search
CPC .............. G01B 11/27; Y10T 29/49826; G01N 21/9501; G01N 2201/025; B25J 15/0616; B25J 15/0666; B25J 15/0658; B24B 37/30
See application file for complete search history.

(56) References Cited

U.S. PATENT DOCUMENTS

| | | | |
|---|---|---|---|
| 5,770,095 A | 6/1998 | Sasaki et al. | |
| 6,032,997 A * | 3/2000 | Elliott | B25B 11/005 269/21 |
| 6,120,360 A | 9/2000 | Ball | |
| 7,654,887 B2 | 2/2010 | Ishikawa et al. | |
| 2001/0024878 A1 | 9/2001 | Nakamura | |
| 2004/0157420 A1 | 8/2004 | Sheydayi | |
| 2005/0103715 A1* | 5/2005 | Sabottke | B01D 61/00 210/650 |
| 2007/0063453 A1* | 3/2007 | Ishikawa | B24B 37/30 279/3 |

FOREIGN PATENT DOCUMENTS

| | | |
|---|---|---|
| JP | 513051 U | 2/1993 |
| JP | H10-128634 A | 5/1998 |
| JP | 2002036102 A | 2/2002 |
| JP | 2002-324831 A | 11/2002 |
| JP | 2004283936 A | 10/2004 |
| JP | 2007-180102 A | 7/2007 |
| JP | 2008-28170 A | 2/2008 |
| TW | 200511379 A | 3/2005 |
| TW | I283889 B | 7/2007 |
| WO | 2004073029 A2 | 8/2004 |
| WO | 2005092564 A1 | 10/2005 |

* cited by examiner

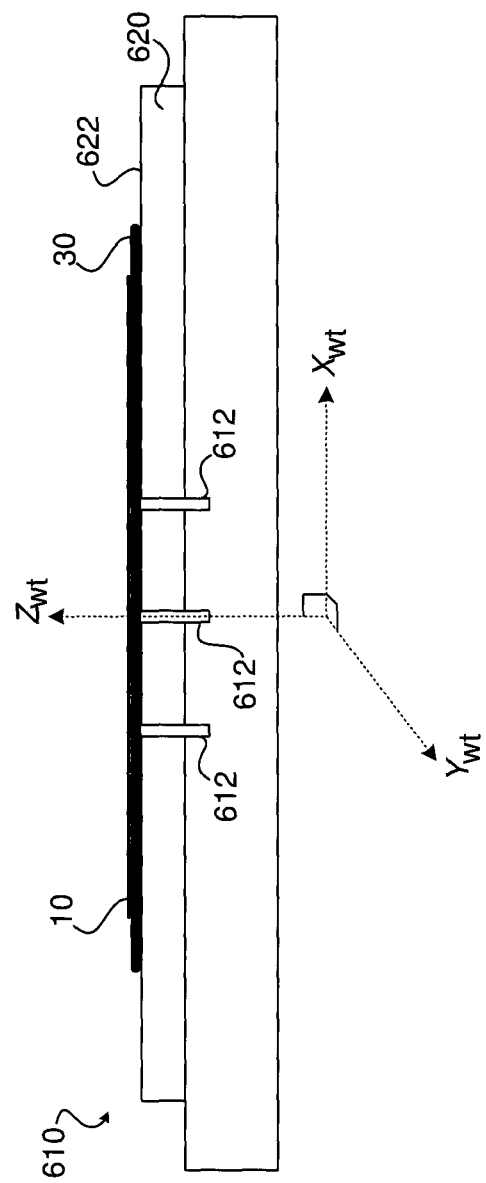

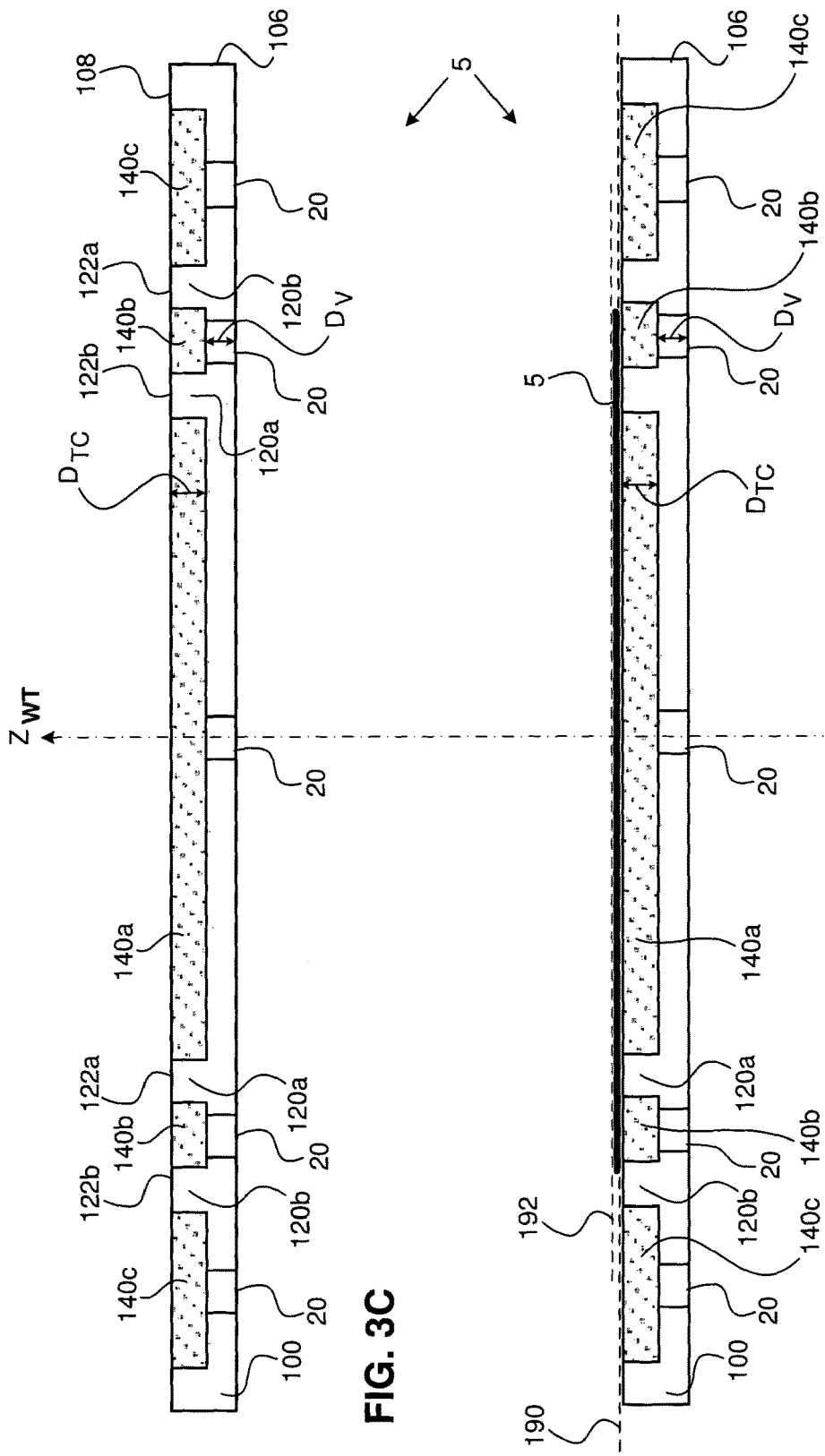

SINGLE ULTRA-PLANAR WAFER TABLE STRUCTURE FOR BOTH WAFERS AND FILM FRAMES

CROSS-REFERENCE TO RELATED APPLICATIONS

This application is a U.S. national stage entry under 35 U.S.C. § 371 of PCT International Patent Application No. PCT/SG2013/000381, filed Sep. 2, 2013, which claims the benefit of U.S. Provisional Patent Application No. 61/696,051, filed Aug. 31, 2012, the contents of which are incorporated herein by reference in their entirety.

TECHNICAL FIELD

The present disclosure relates generally to systems and methods for handling and aligning semiconductor wafers and film frames carrying whole or partial semiconductor wafers. More particularly, aspects of the present disclosure are directed to a single or unified highly planar or ultra-planar porous wafer table structure configured for handling both wafers and film frames in a manner that facilitates accurate, high throughput wafer and/or film frame handling or processing operations, such as optical inspection processes.

BACKGROUND

Semiconductor wafer processing operations involve the performance of various types of processing steps or sequences upon a semiconductor wafer upon which a number of die (e.g., a large or very large number of die) reside. The geometrical dimensions, linewidths, or feature sizes of devices, circuits, or structures on each die are typically very small, for example, micron, submicron, or nanometer scale. Any given die includes a large number of integrated circuits or circuit structures that are fabricated, processed, and/or patterned on a layer-by-layer basis, for instance, by way of processing steps performed upon wafers sitting on planar wafer surfaces, such that the dies carried by the wafer are collectively subjected to the processing steps.

A wide variety of semiconductor device processing operations involve a number of handling systems that perform wafer or film frame handling operations which involve securely and selectively carrying (e.g., transporting, moving, displacing, or conveying) wafers or wafers mounted on film frames (hereafter referred to as "film frame" for brevity) from one position, location, or destination to another, and/or maintaining wafers or film frames in particular positions during wafer or film frame processing operations. For instance, prior to the initiation of an optical inspection process, a handling system must retrieve a wafer or a film frame from a wafer or film frame source such as a wafer cassette, and transfer the wafer or film frame to the wafer table. The wafer table must establish secure retention of the wafer or, film frame to its surface prior to the initiation of the inspection process, and must release the wafer or film frame from its surface after the inspection process is complete. Once the inspection process is complete, a handling system must retrieve the wafer or film frame from the wafer table, and transfer the wafer or film frame to a next destination, such as a wafer or film frame cassette or another processing system.

Various types of wafer handling systems and film frame handling systems are known in the art. Such handling systems can include one or more mechanical or robotic arms configured for performing wafer handling operations which involve the transfer of wafers to and the retrieval of wafers from a wafer table; or performing film frame handling operations which involve the transfer of film frames to and the retrieval of film frames from a wafer table. Each robotic arm includes an associated end effector which is configured for retrieving, picking up, holding, transferring, and releasing a wafer or a film frame by way of the application and cessation of vacuum force relative to portions of the wafer or film frame, in a manner understood by one of ordinary skill in the relevant art.

A wafer table itself can be viewed or defined as a type of handling system, which must reliably, securely, and selectively position and hold a wafer or film frame on a wafer table surface while displacing the wafer or film frame relative to elements of a processing system, such as one or more light sources and one or more image capture devices corresponding to an optical inspection system. The structure of a wafer table can significantly impact whether an inspection system can achieve a high average inspection throughput, as further detailed below. Furthermore, the structure of a wafer table, in association with the physical characteristics wafers and the physical characteristics of film frames, greatly impacts the likelihood that an optical inspection process can reliably generate accurate inspection results.

With respect to the generation of accurate inspection results, during an optical inspection process, a wafer or a film frame must be securely retained upon the wafer table. Additionally, the wafer table must dispose and maintain the upper or top surface of the wafer or film frame in a common inspection plane, such that the surface areas of all wafer die, or as many wafer die as possible, collectively reside in this common plane, with minimum or negligible deviation therefrom. More particularly, the proper or accurate optical inspection of die at very high magnification requires a wafer table to be very flat, preferably with a planarity having a margin of error of less than ⅓ of the depth of focus of the image capture device. If the depth of focus of an image capture device is, for instance, 20 µm, a corresponding wafer table planarity error cannot exceed 6 µm.

For handling die of very small size (eg. 0.5×0.5 mm or smaller) and/or thickness (50 µm or less—e.g., carried by a very thin and/or flexible wafer or substrate), this planarity requirement becomes even more critical. For wafers that are very thin, it is important for the wafer table to be ultra-planar, otherwise it is easy for one or more die on the wafer or film frame to become positioned out of the depth of focus. One of ordinary skill in the art will recognize that the smaller the die, the higher the magnification required, and hence the narrower the band of depth of focus in which the inspection plane must lie.

With such planarity outlined aforesaid, a wafer placed on the wafer table will lie flatly on the wafer table surface, the wafer squeezing out substantially all the air beneath it. The difference in atmospheric pressure between the top and bottom surface of the wafer when the wafer is disposed upon the wafer table results in a large force applied against the top surface of the wafer due to atmospheric pressure, holding the wafer down strongly or reasonably strongly upon the wafer table. As pressure is a function of surface area, the larger the size of the wafer, the greater the force applied downwards on the wafer. This is commonly referred to as the "inherent suction force" or "natural suction force" on the wafer. The flatter the wafer table surface, the greater the natural suction force, up to the limit defined by the finite surface of the wafer. However, the strength of such suction force depends on how flat the wafer table surface is. Some wafer tables are not that flat and may have other grooves or holes on its surface resulting in reduced suction force. As the wafer table will be repeatedly accelerated over short distances during inspection of each die, and a high vacuum force is often applied through the wafer table to the wafer table surface to the underside of the wafer to ensure that the wafer remains as planar as possible and does not move during inspection; this is notwithstanding the presence of such natural suction force.

Various types of wafer table structures have been developed in attempts to securely hold wafers or film frames during wafer or film frame inspection operations, and reliably maintain a maximum number of die in a common plane during inspection operations. However not one design exists that will allow the wafer handling system to handle both wafers and sawn wafers mounted on film frames without one or more of the problems described below. A brief description will be made of each type of existing design and their associated problems.

Several types of wafer chucks have been or are currently in use. In the past, wafers were smaller (e.g., 4, 6, or 8 inches) and significantly thicker (particularly in relation to their overall surface areas, e.g., on a wafer thickness normalized to wafer surface area basis), and each die size was larger. Present-day wafer sizes are typically 12 or 16 inches, yet the thickness of these processed wafers have been decreasing in relation to their increasing size (for instance, thicknesses of 0.70-1.0 mm for 12-inch wafers prior to thinning/backgrinding/backlapping, and 50-150 μm following thinning/backlapping are common), and die sizes (e.g., 0.5-1.0 mm square), respectively. Standard wafer sizes can be expected to further increase over time. Additionally, thinner and thinner wafers can be expected to be processed each year in response to the increasing demands and requirements of electronics and mobile phone manufacturers for thinner die/thinner components to fit into slim-built electronic devices (e.g., flat screen televisions, mobile phones, notebook computers, tablet computers, etc.). As will be explained, these factors contribute to the increasing deficiencies of current designs of wafer table to handle both wafers and film frames.

Historically, and even presently, many wafer chucks have been made of a metal such as steel. Such metal wafer chucks are inlaid with a network of grooves, usually circular grooves that are intersected by grooves radiating linearly from a central location. Through such grooves, vacuum force can be applied to the underside of the wafer, which interfaces with the wafer table surface, in order to facilitate secure retention of the wafer against the wafer table surface. In many wafer table designs, such grooves are arranged in concentric circles of increasing size. Depending on the size of the wafer, one or more grooves would be covered by a wafer when the wafer is disposed upon the wafer table surface. Vacuum can be activated through the grooves covered by the wafer to hold the wafer down during processing operations, such as wafer inspection operations. After inspection, the vacuum is deactivated and ejector pins are deployed to lift the wafer off of the wafer table surface, such that the wafer can be retrieved or removed by an end effector. As there are linear grooves radiating from the centre of the metal wafer table surface, once the vacuum is deactivated, the residual suction force associated with application of the vacuum force to the underside of the wafer is quickly dissipated. Thicker wafers are more amenable to application of significant force applied through the ejector pins to lift the wafer (against any residual suction force, if any) without breaking.

As indicated above, increasingly wafers manufactured today are thinner or much thinner than before (e.g., present wafer thicknesses can be as thin as 50 μm), and each die thereon is also increasingly smaller in size (e.g., 0.5 mm square) than in the past. Technological progression results in smaller die sizes and thinner die, which pose a problem for handling wafers by way of existing wafer table designs. Very often, backlapped/thinned or sawn wafers (hereafter simply "sawn wafers") having die that are very small in size and/or which are very thin are mounted on film frames for processing. Conventional metal wafer tables are not suitable for use with film frames having sawn wafers mounted thereto for a number of reasons.

Bearing in mind that inspection of die involves very high magnification, the higher the magnification, the narrower an acceptable depth of focus band, range, variance, or tolerance will be for accurate inspection. Die that are not in the same plane are likely to be out of the depth of focus of an image capture device. As indicated above, the depth of focus of a modern image capture device for wafer inspection typically ranges from 20-70 μm or smaller, depending on the magnification. The presence of grooves on the wafer table surface presents problems particularly during the inspection of sawn wafers mounted on film frames (with small die sizes) on such systems.

The presence of grooves results in the sawn wafers with small die sizes not sitting properly or uniformly on the wafer table surface. More particularly, in regions where there are grooves (and there can be many), the film frame's film can slightly sag into the grooves, resulting in the whole wafer surface lacking collective or common planarity across all die, which is critical for optical inspection operations. This lack of planarity becomes more pronounced for small or very small die of sawn wafers. Furthermore, the presence of a groove can cause die to be displaced at an angle relative to a common die inspection plane, or cause the die to sag and sit at one or more different and lower planes. Furthermore, light shining on tilted die which have sagged into grooves will reflect light away from the image capture device, such that the capture of an image corresponding to a tilted die will not contain or convey precise details and/or features of one or more regions of interest on the die. This will adversely affect the quality of images captured during inspection, which can lead to inaccurate inspection results.

Several prior approaches have attempted to address the aforementioned problems. For instance, in one approach a metal wafer table support includes a network of grooves. A flat metal plate is placed on top of the network of grooves. The metal plate includes many small or very small vacuum holes that allow vacuum to be applied through the perforations against a wafer or sawn wafer. Depending on the size of wafer under consideration, an appropriate pattern or number of corresponding grooves will be activated. While multiple small or very small vacuum holes can increase the likelihood that die can be collectively maintained in the same inspection plane, collective die planarity problems are still not effectively or completely eliminated due to continuing technological evolution that results in smaller and smaller die sizes and decreasing die thicknesses over time Such designs also include multiple sets of ejector pin triplets corresponding to different wafer sizes, i.e., multiple distinct sets of three ejector pins corresponding to multiple standard wafer sizes that the wafer table is capable of carrying. The presence of numerous holes for ejector pins can also present, and quite possibly worsen, collective die planarity problems when inspecting die carried on film frames, for reasons analogous to those set forth above.

Some manufacturers use wafer table conversion kits, in which a metal wafer table with grooves is used for handling whole wafers, and a metal wafer table cover with many very small openings is used for film frame handling. Unfortunately, conversion kits require inspection system downtime due to the fact that conversion from one type of wafer table to another, and post-conversion wafer table calibration, is time consuming and done manually. Such downtime adversely affects average system throughput (e.g., overall or average throughput with respect to both wafer and film frame inspection operations considered in sequence or together), and hence inspection systems that require wafer table conversion kits are undesirable.

Other wafer table designs, such as described in U.S. Pat. No. 6,513,796, involve a wafer table receptacle that allows for different central wafer table inserts depending on whether wafers or film frames are being processed. For wafer inspection, the insert is typically a metal plate with annular rings having vacuum holes for activation of vacuum. For film frames, the insert is a metal plate having many fine holes for vacuum activation, which can still give rise to collective die nonplanarity as described above.

Still other wafer table designs, such as disclosed in U.S. Patent Application Publication 2007/0063453, utilize a wafer table receptacle having a plate type insert consisting of a porous material in which distinct regions are defined by annular rings made of a thin film material. Typically, such wafer table designs are complex in construct and involves a delicate and complex manufacturing process, and hence difficult, time consuming, or costly to manufacture. Moreover, such designs can utilize metal annular rings to facilitate regional vacuum force control across the wafer table surface in accordance with wafer size. Metal annular rings can require undesirably long planarization times, or damage a polishing device that is used to polish the wafer table surface when planarizing the wafer table surface. Furthermore, metal rings can give rise to nonplanarity due to differential material polishing characteristics across the wafer table surface, and therefore metal annular rings are unsuitable for modern optical inspection processes (e.g., particularly involving sawn wafers mounted on film frames).

Unfortunately, prior wafer table designs are (a) unnecessarily structurally complex; (b) difficult, expensive, or time consuming to fabricate; and/or (c) unsuitable for various types of wafer processing operations (e.g., die inspection operations, particularly when die are carried by a film frame) as a result of insufficient wafer table surface planar uniformity in view of technological evolution that continues to give rise to smaller and smaller wafer die sizes and/or progressively decreasing wafer thicknesses. A need clearly exists for a wafer table structure and an associated wafer table manufacturing technique that that will enable the wafer table to handle both wafers and sawn wafers and which overcomes one or more of the foregoing problems or drawbacks.

SUMMARY

In accordance with an aspect of the present disclosure, a single wafer table structure provides a wafer table surface suitable for handling both wafers and film frames on which wafers or portions thereof are mounted. The wafer table structure includes a base tray comprising a first set of exposed upper surfaces, an interior surface, and a set of compartments formed integrally with or attached to the interior surface, the base tray formed of at least one type of material that is gas or fluid impermeable in response to applied negative pressures; at least one type of compartment material disposed within the set of base tray compartments, the at least one type of compartment material conformable to the set of compartments and hardenable to provide a hardened compartment material in the set of compartments that is gas or fluid permeable in response to applied vacuum forces, and which provides a second set of exposed upper surfaces; and a set of openings formed in the interior surface of the base tray, by which the hardened compartment material is exposable to negative pressures or positive pressures, wherein (a) the first set of exposed upper surfaces of the base tray and (b) the second set of exposed upper surfaces of the hardened compartment material are simultaneously machinable by way of a common machining process to provide a planar wafer table surface (e.g., an ultra-planar surface, exhibiting a planar uniformity across the wafer table surface of +/−100 μm or less) for carrying wafers and film frames. At least one of the base tray and the hardened compartment material comprises a ceramic based material.

A rate at which the first set of exposed upper surfaces of the base tray can be planarized by the common machining process and a rate at which the second set of exposed upper surfaces of the hardened compartment material can be planarized by the common machining process are essentially identical (e.g., to within +/−5-20%, or +/−10%).

The set of compartments can include a plurality of compartments, and the wafer table structure also includes a set of ridges that separates individual compartments within the plurality of compartments from each other. The first set of exposed upper surfaces of the base tray includes exposed upper surfaces of the set of ridges. The base tray and each ridge within the set of ridges can be formed from identical or different materials. The base tray interior surface includes a plurality of inner bottom surfaces. Each ridge within the set of ridges borders an inner bottom surface of the base tray, and each ridge within the set of ridges partitions portions of different base tray inner bottom surfaces from each other to define the set of compartments. Each ridge within the set of ridges and each compartment within the set of compartments is dimensioned in a manner correlated with a standard wafer size and/or a standard film frame size.

In an embodiment, the set of compartments includes a first compartment containing a first volume of hardened compartment material exposed to a first set of openings corresponding thereto; and a second compartment containing a second volume of compartment material exposed to a second set of openings corresponding thereto, the second set of openings distinct from the first set of openings. A first ridge within the set of ridges surrounds the first compartment to thereby separate the first compartment from the second compartment. Negative pressure can be applied to the first set of openings to securely retain a first wafer or first film frame having a first standard diameter to the planar wafer table surface, and wherein negative pressure can be applied to the first set of openings and the second set of openings to securely retain a second wafer or second film frame having a second standard diameter larger than the first standard diameter to the planar wafer table surface.

The set of compartments can also include a third compartment containing a third volume of hardened compartment material exposed to a third set of openings corresponding thereto, the third set of openings distinct from each of the first set of openings and the second set of openings. A second ridge within the set of ridges surrounds the second compartment to thereby separate the second compartment from the third compartment. Negative pressure can be applied to the first set of openings, the second, set of openings, and the third set of openings to securely retain a third wafer or a third film frame having a third standard diameter larger than each of the first and second standard diameters to the planar wafer table surface.

The wafer table structure can also include single set of ejector pin guide members through which a single set of ejector pins can travel for handling wafers of multiple standard sizes.

In accordance with another aspect of the present disclosure, a process for manufacturing a single wafer table structure providing a wafer table surface suitable for handling both wafers and film frames on which wafers or portions thereof are mounted includes: providing a base tray having a first set of exposed upper surfaces, an interior surface, a set of compartments formed integrally with or attached to the interior surface, and at least one set of openings formed in the interior surface, the base tray formed of at least one type of material that is gas or fluid impermeable in response to applied negative pressures; disposing at least one type of compartment material within the set of base tray compartments, the at least one type of compartment material conformable to the set of compartments; hardening the at least one type of compartment material to provide a hardened compartment material in the set of compartments that is gas or fluid permeable in response to applied negative pressures or positive pressures, and which provides a second set of exposed upper surfaces; and simultaneously machining the first set of exposed upper surfaces and the second set of exposed upper surfaces by way of a common machining process to provide a planar wafer table surface for carrying wafers and film frames on which wafers or portions thereof are mounted. During such machining, a rate at which the first set of exposed upper surfaces of the base tray is planarized and a rate at which the second set of exposed upper surfaces of the hardened compartment material is planarized by the common machining process are essentially identical.

BRIEF DESCRIPTION OF THE DRAWINGS

FIG. 1C is a cross-sectional view of the wafer table assembly showing the wafer table and a wafer and/or a film frame securely held along two transverse spatial axes Xwt and Ywt defining a plane, each of which is also transverse to a normal axis Zwt of the wafer table surface.

FIG. 3C is a cross sectional view of a post-planarization process vacuum chuck structure corresponding to the base tray carrying hardened porous ceramic material corresponding to FIGS. 3A and 3B.

FIG. 3D is a cross sectional view of a vacuum chuck structure produced or manufactured in accordance with an embodiment of the present disclosure, which corresponds to FIG. 3C, and which carries a wafer or film frame upon a planar vacuum chuck surface.

DETAILED DESCRIPTION

Figure 1A:
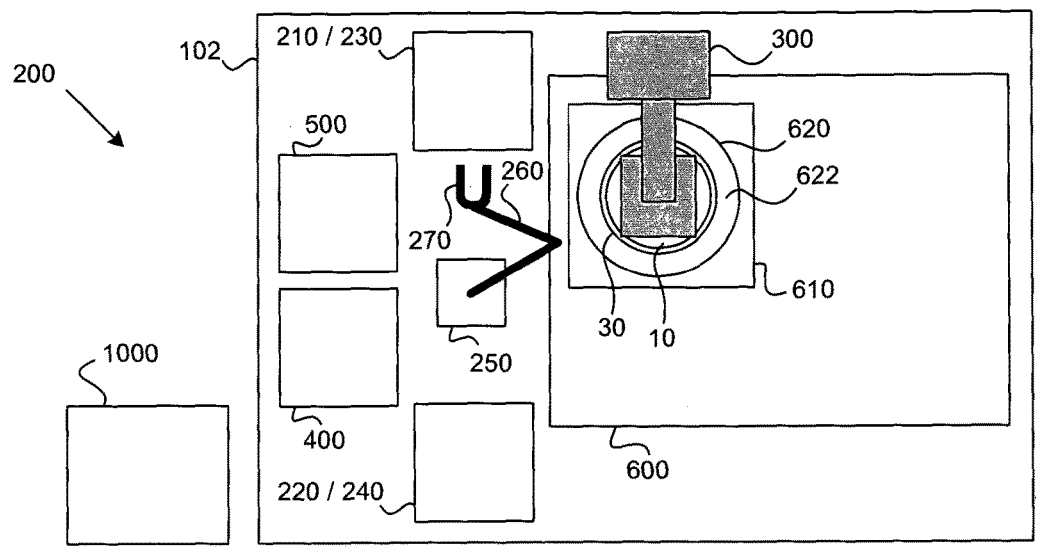
FIG. 1A is a schematic illustration showing portions of a wafer and/or film frame handling system providing a single porous wafer table structure for handling both wafers and film frames in accordance with an embodiment of the present disclosure.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range (e.g., within +/−20%, +/−10%, or +/−5%). Similarly, the recitation of equivalence, essential equivalence, or approximate equivalence is understood to encompass actual equality as well as essential or approximate equivalence (e.g., identical to within +/−20%, +/−10%, or +/−5%).

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

For purpose of brevity and to aid understanding, the term "wafer" as used herein can encompass whole wafers, partial wafers, or other types of whole or partial objects or components (e.g., solar cells) having one or more planar surface areas upon which a set of optical inspection processes and/or other processing operations are desired or required. The term "film frame" in the description that follows generally refers to a support member or frame configured for carrying or supporting a wafer, a thinned or backlapped wafer, or a sawn wafer, for instance, by way of a thin layer or film of material that is disposed or stretched across a film frame surface area, and to which a wafer is mounted or adhered, in a manner understood by one of ordinary skill in the relevant art.

Additionally, the term "wafer table" as used herein includes an apparatus for holding a wafer or a film frame during a wafer inspection process or a film frame inspection process, respectively, where the term "wafer table" will be understood by one of ordinary skill in the relevant art to correspond to or be equivalent, substantially equivalent, or analogous to a wafer chuck, a vacuum table, or a vacuum chuck. The term "non-porous material" as used herein is intended to mean a material that is at least substantially or essentially impermeable to the flow or transfer of a fluid such as air or a liquid therethrough, and which is correspondingly at least substantially or essentially impermeable with respect to the communication or transfer of a negative pressure or vacuum force therethrough (e.g., relative to a given thickness or depth of the non-porous material, such as a depth greater than approximately 0.50-1.0 mm). Analogously, the term "porous material" is intended to mean a material that is at least moderately/substantially or essentially permeable to the flow or transfer of a fluid such as air or a liquid therethrough, and which is correspondingly at least moderately/substantially or essentially permeable with respect to the communication or transfer of a negative pressure or vacuum force therethrough (e.g., relative to a given thickness or depth of the porous material, such as a depth greater than approximately 0.50-1.0 mm). Finally, the terms "ceramic based" and "ceramic based material" in the context of the present disclosure are intended to mean a material that is entirely or substantially ceramic in its material structure and properties.

Embodiments in accordance with the present disclosure are directed to systems and processes for handling wafers and film frames, which provide a single or unified porous wafer table configured for handling both wafers and film frames in a manner that facilitates or enables accurate, high throughput wafer and/or film frame handling or processing operations, such as inspection (e.g. optical inspection) processes.

A highly planar or ultra-planar wafer table in accordance with an embodiment of the present disclosure can be used in association with or form a portion of a system for handling both wafers and film frames, such as an inspection system as further detailed below. While multiple embodiments in accordance with the present disclosure are directed to wafer and film frame inspection systems (e.g., optical inspection systems), several embodiments in accordance with the present disclosure can additionally or alternatively be configured for supporting or performing other types of wafer and/or film frame front end or back end processing operations, such as test operations. Aspects of representative embodiments in accordance with the present disclosure are described in detail hereafter with primary emphasis on inspection systems for purpose of brevity and to aid understanding.

By way of a single or unified wafer table configured for handling both wafers and film frames, embodiments in accordance with the present disclosure eliminate the need for or exclude a wafer table conversion kit, thus eliminating production downtime due to wafer-to-film frame and film frame-to-wafer conversion kit changeover and calibration operations, thereby enhancing average inspection process throughput. A single or unified wafer table in accordance with an embodiment of the present disclosure facilitates or enables high accuracy inspection operations by providing a wafer table surface having a high or very high degree of planarity that maintains wafer die surfaces in a common inspection plane with minimal or negligible deviation therefrom along a direction parallel to a normal axis of the highly planar wafer table surface.

Aspects of a Representative System Configuration and System Elements

FIG. 1A is a block diagram of a system 200 for handing wafers 10 and film frames 30 in accordance with a representative embodiment of the present disclosure, which includes a wafer table assembly 610 couplable to, carrying, or having a single or unified wafer table 620 which provides a wafer table surface 622 exhibiting a high, very high, or ultra-high degree of planarity (e.g., planar to within +/−200 µm, or +/−100 µm, or +/−50 µm) configured for handling both wafers and film frames (e.g., during inspection processes, such as wafer inspection processes and film frame inspection processes, respectively) by an inspection system 600. In a representative non-limiting embodiment, the system 200 further includes a first handling subsystem 250 and a second handling subsystem 300 which are configured for (a) conveying wafers 10 and film frames 30 to and from the inspection system 600. The system 200 can also include additional elements, such as elements configured for (b) providing wafer-to-film frame rotational misalignment correction and wafer non-planarity remediation as part of pre-inspection handling operations, and/or preventing lateral displacement as part of post-inspection handling operations, such as described in U.S. Provisional Patent Application 61/696,051, filed on 31 Aug. 2012, to which the present application claims priority.

Depending upon whether wafers 10 or film frames 30 are being inspected at a given time, the system 200 includes a wafer source 210 such as a wafer cassette, or a film frame source 230 such as a film frame cassette, respectively. Similarly, if wafers 10 are being inspected, the system 200 includes a wafer destination 220 such as a wafer cassette (or a portion of a processing station); and if film frames 30 are being inspected, the system 200 includes a film frame destination 240, which can be a film frame cassette (or a portion of a processing system). A wafer source 210 and a wafer destination 220 can correspond to or be an identical location or structure (e.g., the same wafer cassette). Similarly, a film frame source 220 and a film frame destination 240 can correspond to or be an identical location or structure (e.g., the same film frame cassette).

In the representative embodiment under consideration, the system 200 also includes a wafer pre-alignment or alignment station 400 configured for establishing an initial or pre-inspection alignment of wafers 10 such that wafers 10 are properly aligned relative to the inspection system 600; a rotational misalignment inspection system 500 configured for receiving, retrieving, determining, or measuring a rotational misalignment direction and a rotational misalignment magnitude (e.g., which can be indicated by a rotational misalignment angle) corresponding to wafers 10 mounted upon film frames 30; and a control unit 1000 configured for managing or controlling aspects of system operation (e.g., by way of the execution of stored program instructions), as further detailed below. The control unit 1000 can include or be a computer system or computing device, which includes a processing unit (e.g., a microprocessor or microcontroller), a memory (e.g., which includes fixed and/or removable random access memory (RAM) and read-only memory (ROM)), communication resources (e.g., standard signal transfer and/or network interfaces), data storage resources (e.g., a hard disk drive, an optical disk drive, or the like), and a display device (e.g., a flat panel display screen).

In multiple embodiments, the system 200 additionally includes a support structure, base, underframe, or undercarriage 202 that is coupled to or configured for supporting or carrying at least the second handling subsystem 300 such that the second handling subsystem 300 can operatively interface with the first handling subsystem 250 and the processing system 600 to facilitate wafer or film frame handling operations. In some embodiments, the support structure 202 supports or carries each of the first handling subsystem 250, the second handling subsystem 300, the wafer alignment station 400, the misalignment inspection system 500, and the inspection system 600.

Figure 1B:
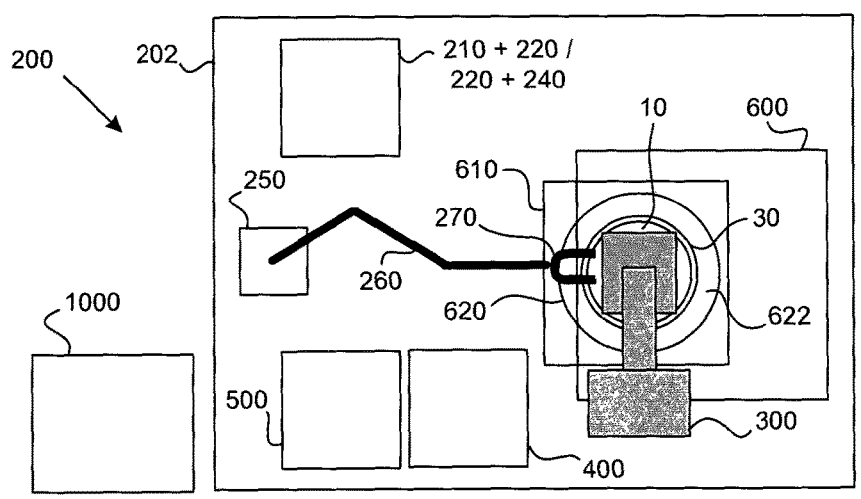
FIG. 1B is a schematic illustration showing portions of a wafer and/or film frame handling system providing a single porous wafer table structure for handling both wafers and film frames in accordance with an embodiment of the present disclosure.

FIG. 1B is a block diagram of a system 200 for handing wafers 10 and film frames 30 which provides a single or unified wafer table 620 configured for handling both wafers and film frames during inspection by an inspection system 600, and which further provides a first handling subsystem 250 and a second handling subsystem 300 in accordance with another embodiment of the present disclosure. In this embodiment, a wafer source 210 and a wafer destination 230 are identical, e.g., the same wafer cassette; and a film frame source 220 and a film frame destination 240 are identical, e.g., the same film frame cassette. Such an embodiment can provide a smaller or significantly reduced spatial footprint, resulting in a compact, space efficient system 200.

In a further representative embodiment, the inspection system 600 is configured for performing 2D and/or 3D optical inspection operations upon wafers 10 and film frames 30. An optical inspection system 600 can include a number of illumination sources, image capture devices (e.g., cameras) configured for capturing images and generating image data sets corresponding thereto, and optical elements configured for some or each of directing illumination toward wafers 10, directing illumination reflected from wafer surfaces toward particular image capture devices, reflecting or optically affecting (e.g., filtering, focusing, or collimating) illumination incident upon and/or reflected from wafer surfaces, in a manner understood by one of ordinary skill in the relevant art. The optical inspection system 600 also includes or is configured for communication with a processing unit and a memory for analyzing image data sets by way of the execution of stored program instructions, and generating inspection results. As previously indicated, the system 600 can include or alternatively be another type of processing system.

With further reference to FIG. 1C, the wafer table 620 carried by the wafer table assembly 610 provides a highly planar or ultra-planar external or exposed wafer table surface 622 onto or upon which wafers 10 as well as film frames 30 can be disposed or positioned and securely held or retained, such that wafer die 12 are collectively maintained in a common inspection plane with minimum or negligible planar deviation therefrom, along a direction parallel to a normal axis $Z_{wt}$ of the highly planar wafer table surface 622 defined normal to a midpoint, center, centroid, or approximate midpoint, center, or centroid of the wafer table surface 622. The wafer table assembly 610 is configured for selectively and controllably displacing the wafer table 620, and hence any wafer 10 or film frame 30 carried or securely held thereby, along two transverse spatial axes corresponding to or defining a plane, for instance, wafer table x and y axes $X_{wt}$ and $Y_{wt}$, respectively, each of which is also transverse to axis $Z_{wt}$.

The wafer table 620 is configured for selectively and securely holding or retaining wafers 10 or film frames 30 upon or against the wafer table surface 622 by way of (a) an inherent or natural suction force that exists due to a pressure differential between atmospheric pressure acting upon the wafer's top, upper, or exposed surface and the wafer's bottom or underside, in combination with (b) the selectively controlled application of vacuum force or negative pressure to the underside of the wafer 10. The wafer table 620 can further be configured for applying or delivering positive air pressure to a wafer 10 or a film frame 30, for instance, by applying a brief/momentary, e.g., approximately 0.50 second, or 0.25-0.75 second, spurt of positive air pressure, e.g., an air purge or air puff, to an interface between the wafer table surface 622 and the underside of wafers 10 or film frames 30 to facilitate the release of vacuum suction acting on the wafers 10 or film frames 30 from the wafer table surface 622 following the interruption or cessation of an applied vacuum force.

In various embodiments, the wafer table assembly 610 includes a set of ejector pins 612 that can be selectively and controllably displaced in a perpendicular or vertical direction relative to the wafer table surface 622, parallel to or along the wafer table z axis $Z_{wt}$ for vertically displacing wafers 10 or film frames 30 relative to the wafer table surface 622. In multiple embodiments, the wafer table 620 includes a single set of ejector pins 612 (e.g., three ejector pins) configured for handling wafers 10 of multiple standard sizes, such as 8, 12, and 16 inch wafers 10. The wafer table 620 need not include, and can omit or exclude, additional sets of ejector pins 612 (e.g., additional sets of three ejector pins), due to the positioning of the single set of ejector pins 612 upon the wafer table 620 (e.g., positioned to carry 8-inch wafers somewhat near, generally near, near, or proximate to their periphery) and the manner in which wafers and film frames are handled in accordance with embodiments of the present disclosure. As further detailed below, in several embodiments, while ejector pins 612 can be used in association with the transfer of wafers 10 to and from the wafer table 620, the transfer of film frames 30 to and/or from the wafer table 620 need not involve, and can omit or entirely exclude, the use of ejector pins 612.

In multiple embodiments, the wafer table 620 includes or has a structure that is identical, essentially identical, substantially identical, or analogous to a wafer table structure described hereafter with reference to FIG. 2A-FIG. 7.

Aspects of a Representative Unified Wafer Table Structure for Wafer and Film Frame Handling In embodiments in accordance with the present disclosure, a wafer table structure can include a base tray (or base receptacle, frame, form, repository, or reservoir structure) having a number of ridges (which can include or be protrusions, ridges, raised strips, partitions, corrugations, creases, or folds) formed integrally from or attached to an interior or base surface of the wafer table structure (e.g., the bottom of base tray). In various embodiments, the base tray can includes at least one type of non-porous material, such as a ceramic based material. The base tray is intended to be gas or fluid (e.g., air) impermeable, or essentially gas or fluid impermeable, in response to application of vacuum force(s). That is, the non-porous material is intended to be impervious or essentially impervious to the passage of gas, fluid, or vacuum force(s) therethrough in response to applied vacuum force(s). The non-porous material is further intended to be easily or readily machinable, grindable, or polishable by ordinary techniques and equipment, such as conventional polishing wheels. In multiple embodiments, the non-porous material can include or be porcelain.

The ridges define, delineate, divide, or separate the base tray into multiple compartments, chambers, cell structures, open regions, or recesses into which at least one type of moldable, formable, conformable, or flowable porous material can be introduced, provided, deposited, or poured and cured, solidified, or hardened. The porous material can further be securely bonded (e.g., chemically bonded, such as in association with a hardening, solidification, or curing process) or adhered to the base tray compartments, such that the hardened porous material is securely retained within or joined to the compartments. Additionally or alternatively, the ridges can be shaped in such a way such that the porous material when hardened or cured within the compartments is secured or retained therein by the structure of the ridges. The ridges can be structured to include curved and/or overhanging portions, or take other suitable shapes, as desirable or required.

The porous material in the compartments is intended to permit the passage of gas or fluid (e.g., air) in response to the application of vacuum force(s) thereto, such that gas, fluid, or vacuum force(s) can be communicated or transmitted therethrough (e.g., after it has been cured or hardened, and vacuum force(s) are applied thereto). Furthermore, the porous material is intended to be easily or readily machinable, grindable, or polishable by ordinary techniques and equipment, such as conventional polishing wheels.

The choice of non-porous base tray material(s), and/or porous material(s) for introduction into base tray compartments, for the wafer table structure depends upon the desired or required characteristics of the wafer table structure in relation to the application or process that is to be carried out on a wafer 10 or film frame 30 residing thereon. For instance, optical inspection of small or ultra-small die 12 on large diameter sawn wafers 10 carried by film frames 30 requires that the wafer table structure provide a wafer table surface having a very high or ultra-high degree of planarity. Moreover, the choice of non-porous base tray material(s) and/or porous compartment material(s) can depend upon the chemical, electrical/magnetic, thermal, or acoustic requirements that the wafer table structure should meet in view of the expected or intended types of wafer or film frame processing conditions to which the wafer table structure will be exposed.

In various embodiments, the non-porous base tray material(s) and the porous compartment material(s) are selected based on material characteristic(s) or quality(ies) that will facilitate or enable the grinding or polishing across multiple exposed surfaces of at least two distinguishable or different materials by a single grinding or polishing apparatus (e.g., substantially or essentially simultaneously). More particularly, exposed surfaces of the two (or more) distinguishable or different non-porous and porous materials can be simultaneously machined; grinded, or polished in the same or an identical manner, such as by way of a single, common, or shared process that involves standard machining, grinding, or polishing equipment operating or operated in accordance with standard machining, grinding, or polishing techniques. Such machining, grinding, or polishing of each of the non-porous and porous materials results in low, minimal, or negligible damage to machining, grinding, or polishing elements, devices, or tools such as polishing heads. Furthermore, in a number of embodiments, the non-porous base tray material(s) and porous compartment material(s) are selected such that a rate at which the non-porous base tray material(s) are affected (e.g., planarized) by such machining, grinding, or polishing and the rate at which the porous compartment material(s) is/are affected (e.g., planarized) by such machining, grinding, or polishing are substantially or essentially identical.

For purpose of brevity and ease of understanding, in the representative embodiments of wafer table structures described below, the non-porous base tray material includes or is a non-porous ceramic based material, and the porous compartment material includes or is a porous ceramic based material. One of ordinary skill in the relevant art will understand that a wafer table structure in accordance with an embodiment of the present disclosure is not limited to the material types provided in relation to the representative embodiments described below.

When the creation of a very flat, highly planar, or ultra-planar wafer table surface is desired or required, the porous material can include a moldable porous based ceramic material and/or other chemical compound which is suitable for forming, fabricating, or manufacturing a porous wafer table, wafer chuck, vacuum table, or vacuum chuck in accordance with standard/conventional processing techniques, processing sequences and processing parameters (e.g., hardening temperatures or temperature ranges, and corresponding hardening times or time intervals), in a manner understood by one of ordinary skill in the relevant art. In multiple embodiments, the porous material can include or be a commercially available material provided by CoorsTek (CoorsTek Inc., Hillsboro, Oreg. USA, 503-693-2193). Such a porous material can include or be one or more types of ceramic based materials, such as Aluminum Oxide (Al2O3) and Silicon Carbide (SiC), and can exhibit a post-hardened/post-cured pore size between approximately 5-100 μm (e.g., about 5, 10, 30, or 70 μm), and a porosity ranging between approximately 20-80% (e.g., about 30-60%). The pore sizes of the porous compartment material(s) can be selected based upon application requirements, such as an intended or desired level of vacuum force suitable for an application under consideration (e.g., the inspection of thin or very thin wafers 10 on film frames 30), as will be understood by one of ordinary skill in the art.

Exposed, upper, or outer surfaces corresponding to portions of the ceramic base tray (e.g., the set of ridges, and possibly an outer base tray border) and hardened moldable porous ceramic material carried by base tray compartments can be machined (e.g., by way of a unified or single machining or polishing process) to provide a common wafer table surface exhibiting a very high or ultra-high degree of planarity or planar uniformity, which is suitable for securely retaining wafers or film frames in a manner that effectively disposes or maintains the wafer die surfaces along or within a common plane (perpendicular to the normal axis of the wafer table surface) with minimal or negligible deviation therefrom, e.g., during inspection.

Figure 2A:
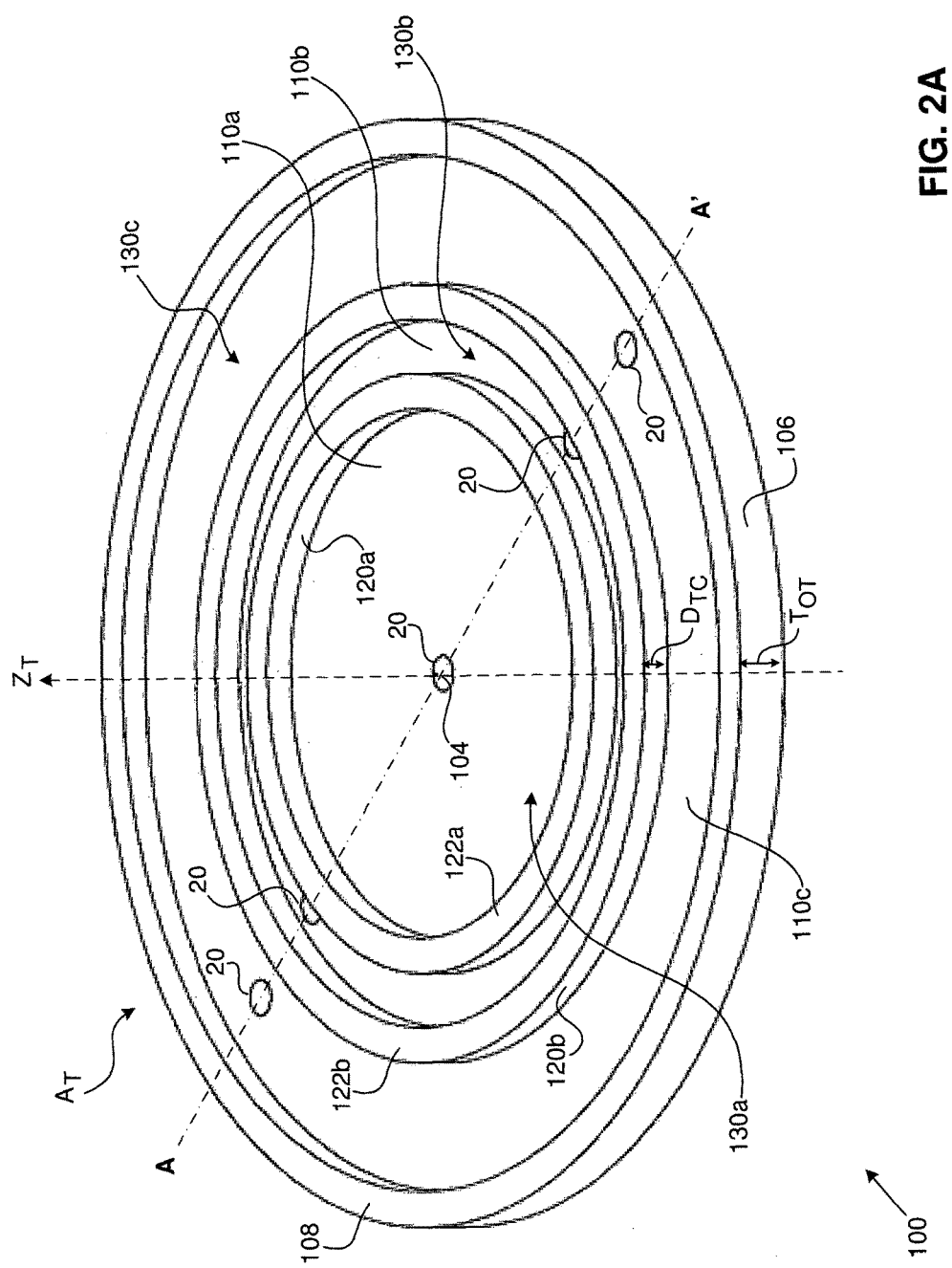
FIG. 2A is a perspective view of a wafer table base tray that includes a non-porous material, such as a ceramic based non-porous material, in accordance with an embodiment of the present disclosure.
Figure 2B:
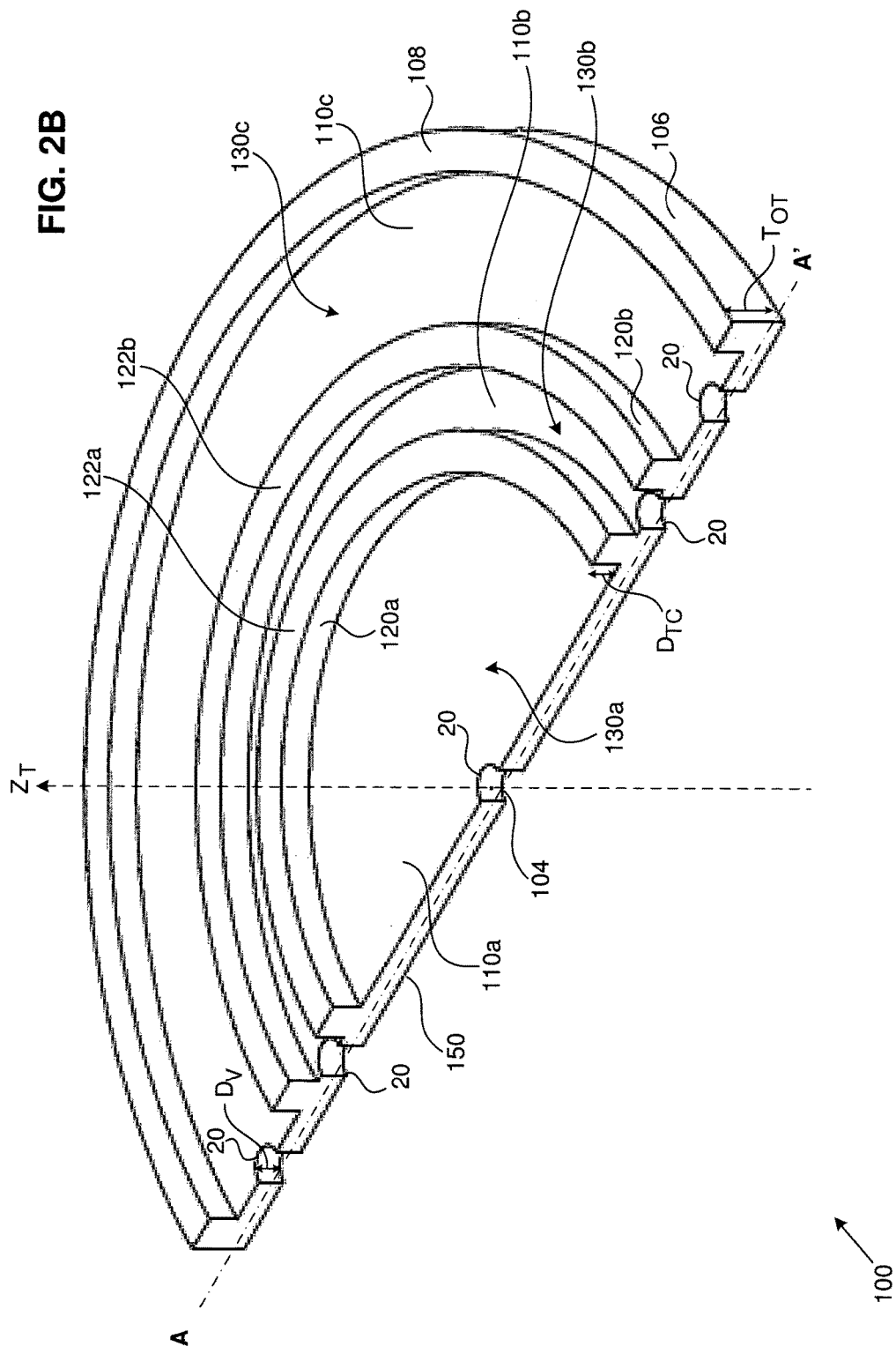
FIG. 2B is a perspective cross sectional view of the base tray of FIG. 2A, taken through a line A-A'.

FIG. 2A is a perspective view of a ceramic based base tray 100, and FIG. 2B is a perspective cross sectional view of the base tray of FIG. 2A, taken through line A-A', in accordance with an embodiment of the disclosure. As indicated above, in various embodiments the ceramic based base tray 100 is non-porous or essentially non-porous, and hence is impervious or essentially impervious with respect to gas, fluid, or vacuum force transfer therethrough in response to applied vacuum force(s). That is, the ceramic based base tray 100 is typically intended to serve as a strong, very strong, or effectively impenetrable barrier relative to the communication or transfer of gas, fluid, or vacuum force(s) therethrough.

In an embodiment, the base tray 100 has a shape that defines a center or centroid 104, relative to or surrounding which a vacuum opening 20 can be disposed; a planar or transverse spatial extent or area $A_T$; an outer periphery or border 106; a plurality of inner bottom surfaces 110a-c, which can include a number of vacuum openings 20 disposed therein; and one or more ridges 120a-b disposed between the base tray's center and its outer border 106 (e.g., in an annular or concentric arrangement). As further detailed below, in various embodiments the ridges 120a-b, as well as the base tray's outer border 106, are sized, shaped, and/or dimensioned in a manner correlated with or corresponding to standard wafer and/or film frame sizes, shapes, and/or dimensions (e.g., 8-inch, 12-inch, and 16-inch wafers, and one or more film frame sizes corresponding to such wafer sizes). The base tray 100 further includes at least one underside surface 150, significant portions or the entirety of which in a number of embodiments are disposed or substantially disposed in a single base tray underside plane.

In several embodiments, a vertical base tray axis $Z_T$ can be defined perpendicular or substantially perpendicular to the base tray's underside surface 150 and the base tray's inner bottom surfaces 110a-c, and extending through the base tray's center or centroid 104. As will be understood by one of ordinary skill in the relevant art, the vertical base tray axis $Z_T$ is defined perpendicular to an intended wafer table planar surface upon or against which a wafer or film frame can be securely held or retained. In FIGS. 2A and 2B, $Z_T$ can be perpendicular to the line A-A', which bisects each vacuum opening 20.

Each ridge 120a-b borders inner bottom surfaces 110a-c of the base tray 100, and each ridge 120a-b delineates, separates, or partitions portions of different base tray inner bottom surfaces 110a-c from each other to define a set of base tray compartments or receptacles 130a-b that can receive or carry the aforementioned moldable, formable, conformable, or flowable porous material. More particularly, in the embodiment shown in FIG. 2A, a first ridge 120a extends above and surrounds (e.g., concentrically surrounds) a first inner bottom surface 110a of the base tray 100. A contiguous or generally contiguous structural recess defined by the first ridge 120a surrounding or encircling the first inner bottom surface 110a thereby defines a first base tray compartment or receptacle 130a, which has as its bottom surface the first inner bottom surface 110a. In an analogous manner, the first ridge 120a and the second ridge 120b extend above a second inner bottom surface 110b of the base tray 100. The second ridge 120b encloses the first ridge 120a (e.g., the first and second ridges 120a-b are concentric relative to each other), such that the first and second ridges 120a-b define a second contiguous or generally contiguous base tray compartment or receptacle 130b having as its bottom surface the second inner bottom surface 110b. Also analogously, the base tray's outer border 106 encloses the second ridge 120b (e.g., the second ridge 120b and the outer border 106 are concentric relative to each other), such that they define a third contiguous or generally contiguous base tray compartment or receptacle 130c having as its bottom surface the third inner bottom base tray surface 110c. Any given ridge 120 has a transverse ridge width, for instance, approximately 1-4 mm (e.g., approximately 3 mm); and a corresponding ridge depth, for instance, approximately 3-6 mm (e.g., approximately 4 mm) which defines the depth of a compartment or receptacle 130. As further described below, in various embodiments, any given base tray compartment or receptacle 130a-c has a spatial extent, planar surface area, or diameter that is correlated with or corresponds to the spatial extent, planar surface area, or diameter of standard wafer and/or film frame sizes, shapes, and/or dimensions.

Similar or analogous considerations to the foregoing apply to the definition of additional or other types of base tray compartments or receptacles 130 in alternate embodiments, including embodiments having a single ridge 120; embodiments having more than two ridges 120a-b; and/or embodiments in which portions of one or more ridges 120 do not fully enclose one another, or are not annular/concentric with respect to one or more other ridges 120 (e.g., when portions of a particular ridge 120 are transversely, radially, or otherwise disposed with respect to another ridge 120). The manner in which ridges 120 exhibiting various shapes, sizes, dimensions, and/or segments (e.g., a ridge 120 can include multiple distinct or separate segments or sections disposed with respect to an elliptical, circular, or other type of geometric outline or pattern) can define different types of base tray compartments or receptacles 130 will be readily understood by one of ordinary skill in the relevant art.

In addition to the foregoing, the base tray's outer border 106 as well as each ridge 120a-b respectively includes an exposed outer border upper surface 108 and an exposed ridge upper surface 122a-b, corresponding to an upper surface or upper side of the base tray 100 that, relative to the base tray's underside surface 150, is intended to be closest to a wafer 10 or film frame 30 carried by a wafer table planar surface. In multiple embodiments, a vertical distance (e.g., parallel to the base tray's central transverse axis $Z_T$) between the base tray's outer border upper surface 108 and the base tray's inner bottom surfaces 110a-c, as well as between each ridge upper surface 122a-b and the base tray's inner bottom surfaces 110a-c, defines a base tray compartment depth $D_{TC}$. A vertical distance between the base tray's outer border upper surface 108 and the base tray's underside surface 150 defines an overall base tray thickness $T_{OT}$. Finally, a vertical distance along which a vacuum opening 20 extends can define a vacuum passage depth $D_V$, which is equal to the difference between $T_{OT}$ and $D_{TC}$.

Figure 3A:
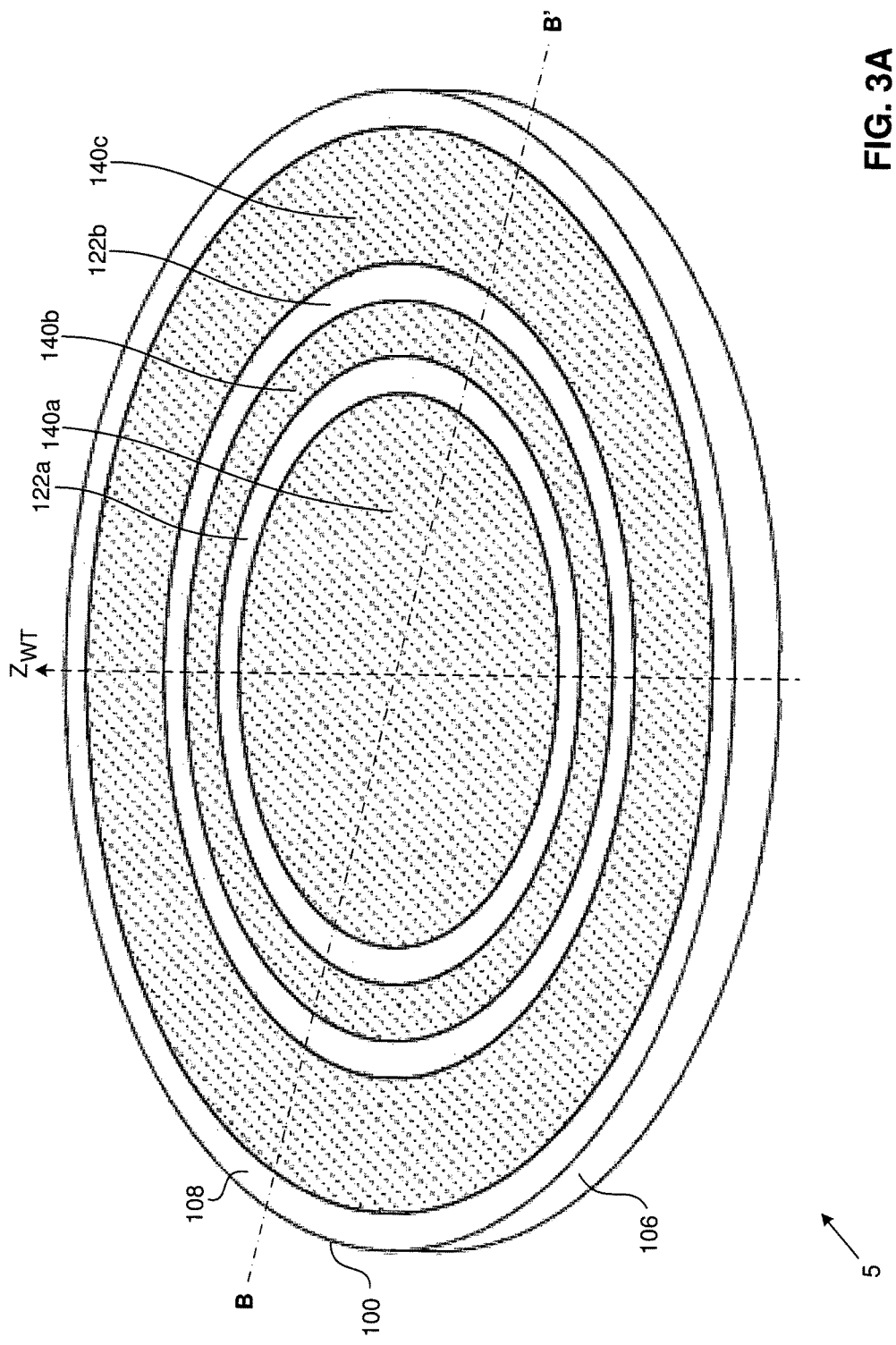
FIG. 3A is a perspective view of the base tray of FIG. 2A into which a moldable, formable, conformable or flowable porous material, such as a ceramic based porous material, has been disposed.
Figure 3B:
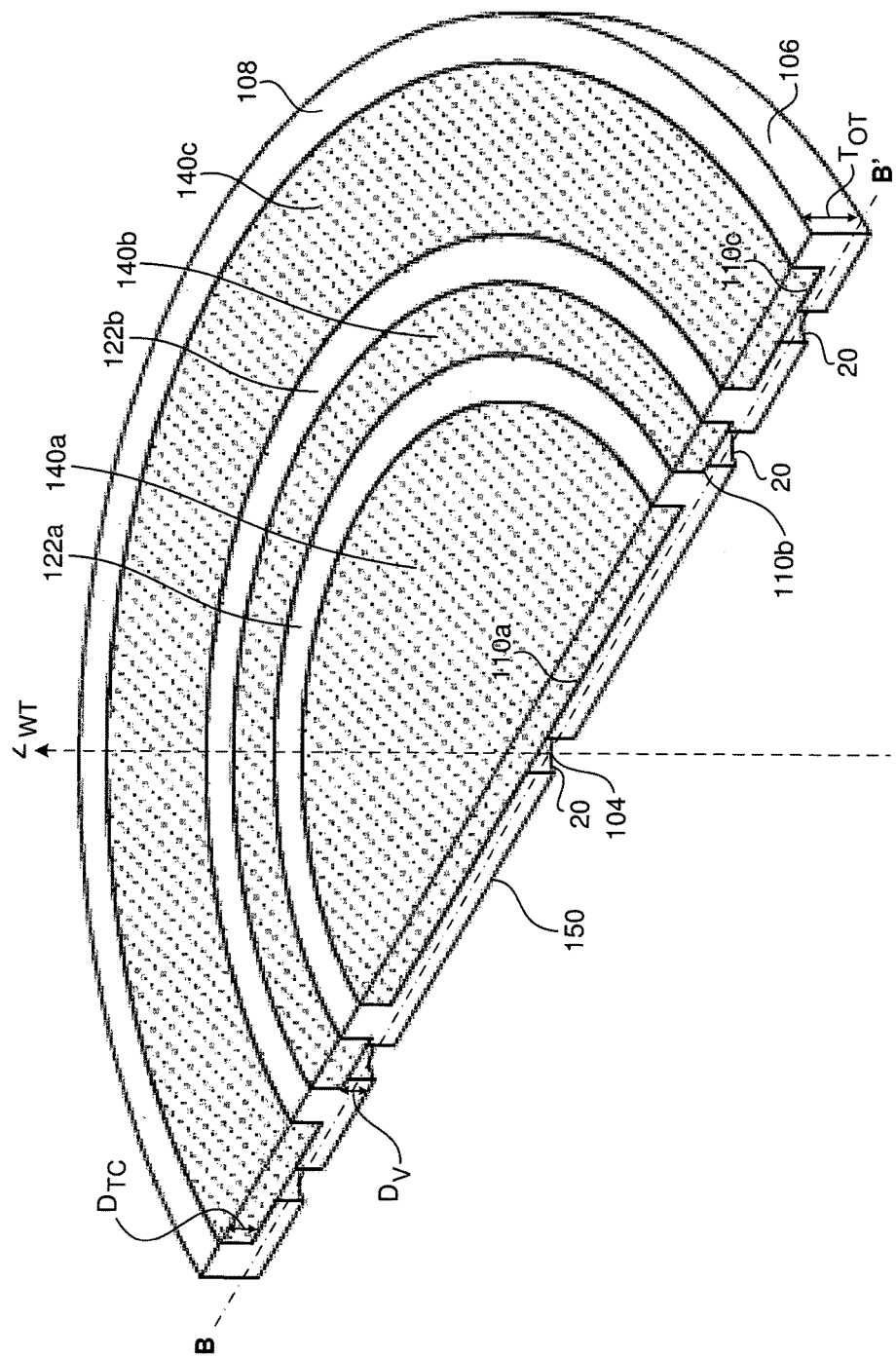
FIG. 3B is a perspective cross sectional view of the base tray carrying the moldable, formable, conformable, or flowable porous ceramic based material corresponding to FIG. 3A, taken through a line B-B'.

FIG. 3A is a perspective view of the base tray 100 of FIG. 2A into which a moldable, formable, conformable, or flowable porous material has been introduced, disposed, or provided to effectively provide the basis for, facilitate or effectuate the formation of, or form a wafer table structure 5 in accordance with an embodiment of the present disclosure. FIG. 3B is a perspective cross sectional view of the base tray 100 carrying the porous material corresponding to FIG. 3A, taken through the line B-B'. FIG. 3C is a cross sectional view of the base tray 100 carrying the porous material corresponding to FIGS. 3A and 3B.

In FIGS. 3A and 3B, the porous material can be considered to be resident within the base tray compartments 130a-c in a pre-hardened/pre-set or post-hardened/post-set state, depending upon a stage of wafer table structure fabrication under consideration. Furthermore, if considered in a post-hardened/post-set state, the porous material and the non-porous or vacuum impervious ceramic based base tray 100 can be considered in a pre-planarized/pre-machined or post planarized/post-machined state, once again depending upon a wafer table structure fabrication stage under consideration. Stages of a representative wafer table structure fabrication process in accordance with an embodiment of the present disclosure are described in detail below.

Figure 4A:
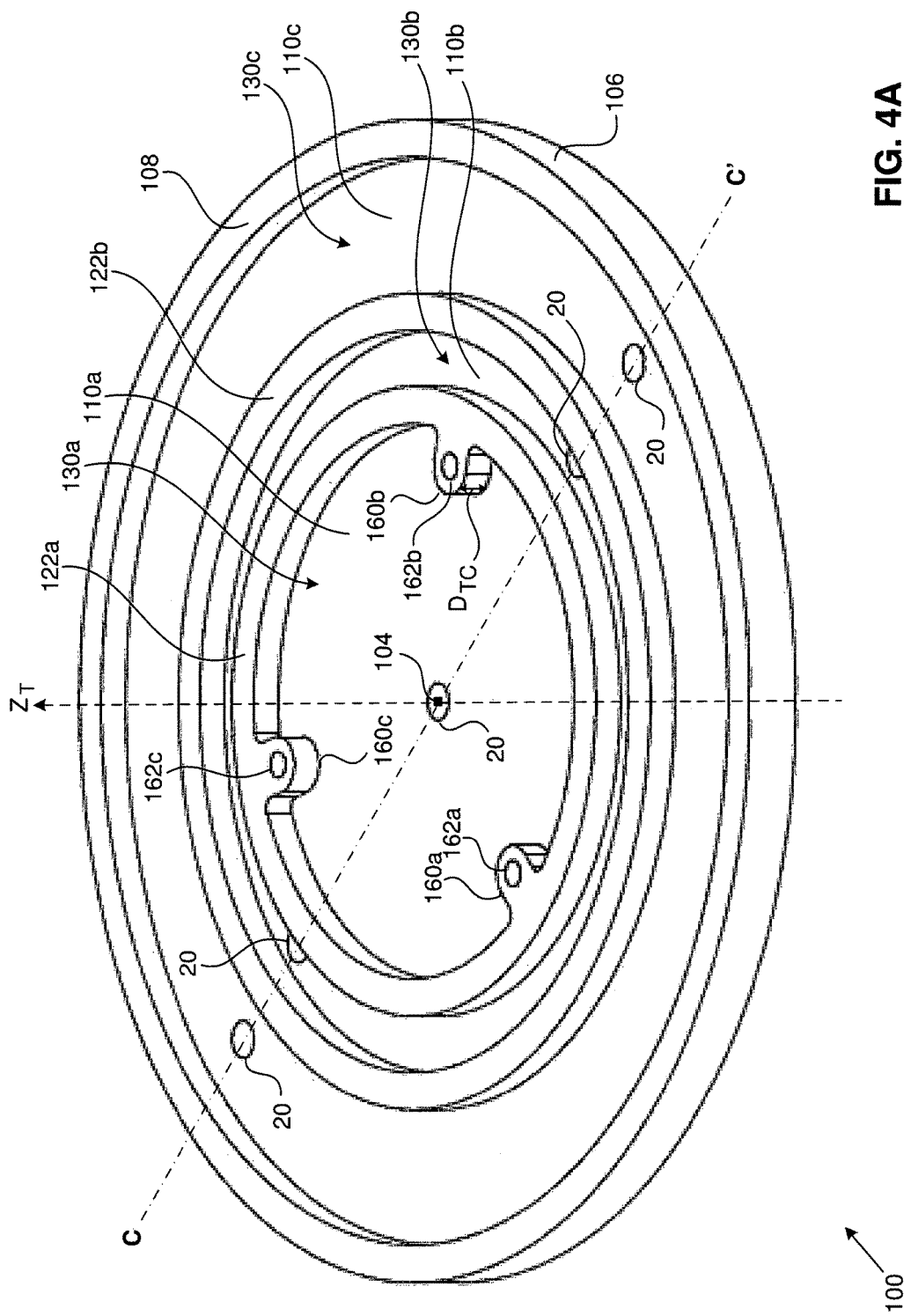
FIG. 4A is a perspective view of a ceramic based vacuum chuck base tray in accordance with another embodiment of the present disclosure, which includes a set of ejector pin guide members.
Figure 4B:
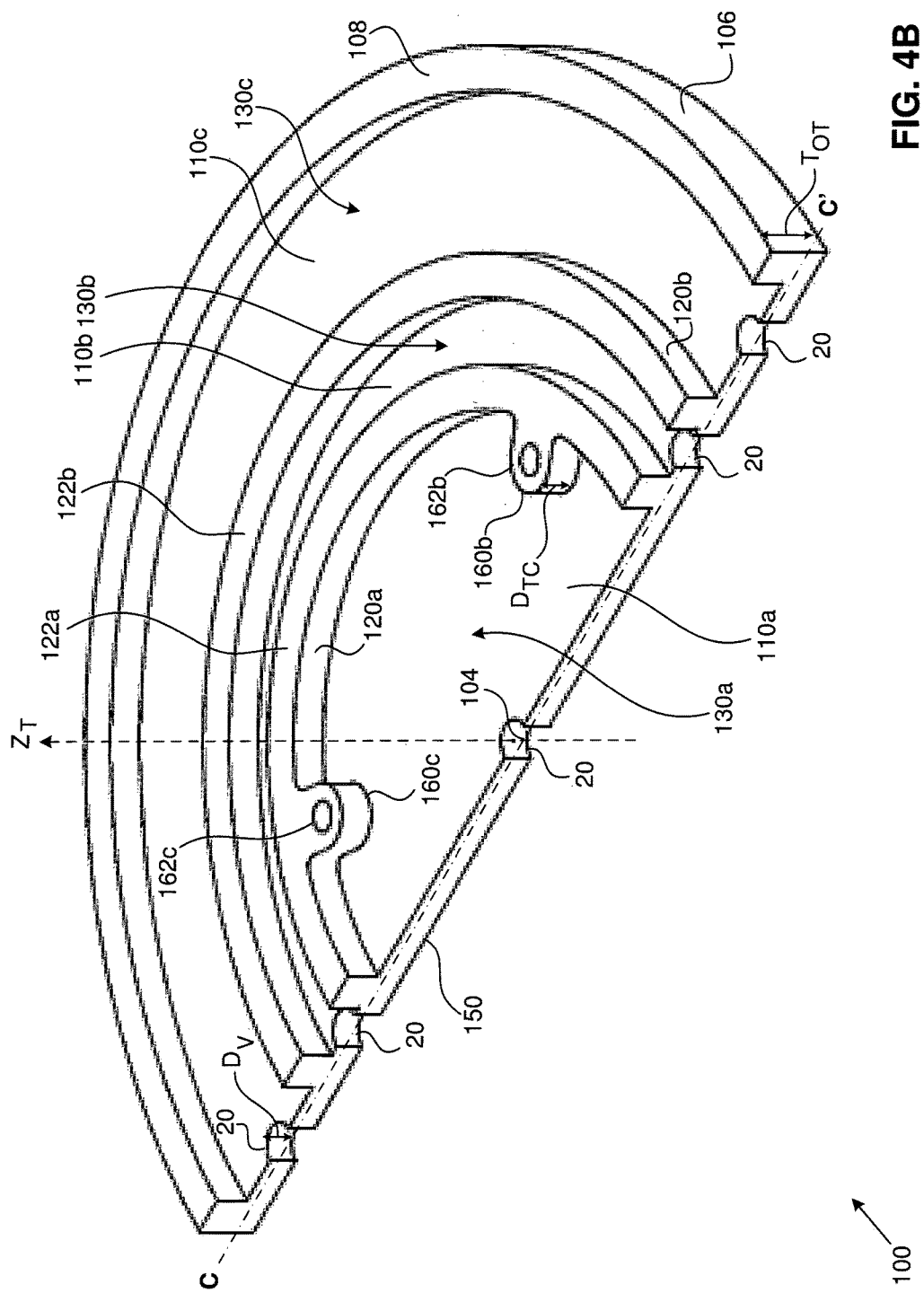
FIG. 4B is a cross-sectional view of the ceramic based vacuum chuck base tray of FIG. 4A, taken thorough a line C-C'.

In view of FIGS. 3A-3C and relative to the base tray embodiment shown in FIGS. 2A and 4B, following the introduction, placement, deposition, or provision of the porous material into the base tray compartments 130a-c and the conformation of the porous material to the internal geometry of the base tray compartments 130a-c, the first base tray compartment 130a is filled by a first volume 140a of porous material; the second base tray compartment 130b is filled by a second volume 140b of porous material; and the third base tray compartment 130c is filled by a third volume 140c of porous material. Analogous or similar considerations apply to other base tray embodiments having different numbers and/or configurations of compartments 130. That is, after the porous material has been introduced into base tray compartments 130, each of such compartments 130 is filled with a given volume 140 of the porous material corresponding to the dimensions or volumetric capacity of any given compartment 130 under consideration. An initial volume 140 of porous material introduced into any given base tray compartment 130 should equal or exceed the compartment's volume, such that excess porous material can be machined or polished away in association with a planarization process, as further detailed below.

After the introduction of the porous material into a compartment 130, portions of any given volume 140 of porous material are exposed to a number of vacuum openings 20 within the compartment 130. More particularly, within a given volume 140 of porous material, porous material that interfaces with a base tray inner bottom surface 110 are selectively exposed to one or more vacuum openings 20 disposed or formed within a corresponding base tray inner bottom surface 110. For instance, as more particularly indicated in the embodiment shown in FIGS. 3B and 3C, the first volume 140a of porous material is exposed to the vacuum opening 20 disposed at the center of the base tray 100 within the first inner bottom surface 110a of the first base tray compartment 130a. Analogously, the second volume 140b of porous material is exposed to the vacuum openings 20 disposed within the second inner bottom surface 110b of the second base tray compartment 130b; and the third volume 140c of porous material is exposed to the vacuum openings 20 disposed within the third inner bottom surface 110c of the third base tray compartment 130c. Because each volume 140a-c of porous material is exposed to a corresponding set of vacuum openings 20, vacuum force(s) can be selectively communicated, distributed, or transferred through each volume 140a-c of porous material, to the upper surface of the porous material corresponding to the upper surface of the wafer table structure 5. Hence, when the wafer table structure 5 carries a wafer 10 or film frame 30 of a particular size or shape upon a planar wafer table surface, vacuum force(s) can be selectively communicated or transferred to the underside of a wafer 10 or film frame 30 through the corresponding base tray compartments covered by the wafer 10 or film frame 30 disposed upon a wafer table planar surface, as further elaborated upon below.

As indicated above and further elaborated upon below, after the porous material volumes 140 have been introduced into the base tray compartments 130, each such volume 140 can be hardened, solidified, or cured and bonded (e.g., collectively, in association or simultaneous with a hardening/bonding process) to an interior bottom surface 110 and associated side surfaces or sidewalls of one or more ridges 120 that define a compartment 130. Additionally, following a hardening/bonding process, exposed upper surfaces of the wafer table structure 5, which include exposed upper surfaces of the volumes 140 of porous material, exposed ridge upper surfaces 122, and the exposed outer border upper surface 108 can be simultaneously machined, polished, or planarized by way of one or more conventional, technologically simple, inexpensive, and robust machining or polishing techniques or processes using a single machining, grinding, or polishing apparatus across two distinguishable or different material surfaces. Furthermore, the use of single machining, grinding, or polishing apparatus gives rise to, provides, or defines a wafer table planar surface that exhibits a very high or ultra-high degree of planar uniformity. As a result, die 12 carried by a wafer 10 or film frame 30 disposed and securely held or retained upon the wafer table planar surface are maintained in a common plane in a manner that effectively maintains the upper or exposed die surfaces in said common plane with minimal or negligible deviation therefrom, even for very small die and/or very thin wafers. The upper surfaces of such die 12 therefore exhibit minimal or negligible positional deviation out of said common plane, along a direction parallel to a normal axis of the highly planar wafer table surface (e.g., a wafer table vertical axis $Z_{WT}$ corresponding to, overlapping with, or subsuming the base tray's vertical axis $Z_T$). The ultra-high planarity of the wafer table surface provided by multiple embodiments in accordance with present disclosure enables the die 12 on wafers 10 or film frames 12 residing on the wafer surface to sit substantially in/on one single plane (e.g., an inspection plane) to facilitate accurate inspection and/or other processing.

FIG. 3D is a cross sectional view of a wafer table structure 5 produced or manufactured in accordance with an embodiment of the present disclosure, which corresponds to FIG. 3C, and which and which carries a wafer or film frame upon a planar wafer table surface. The wafer table structure 5 provides a wafer table planar surface 190 having a very high or ultra-high degree of planar uniformity, such that die 12 (e.g., very small and/or very thin die 12), devices, or material layers carried by a wafer 10 or film frame 30 that is securely held or retained upon the wafer table planar surface by way of vacuum force(s) are collectively or commonly maintained, essentially maintained, or very substantially maintained in a wafer or film frame processing plane 192 (e.g., an optical inspection plane) with minimal or negligible positional deviation or displacement away from or out of the wafer or film frame processing plane 192 in a direction along a wafer table vertical axis $Z_{WT}$ (or equivalently, in a direction toward or away from the wafer table planar surface 190). In a representative embodiment, exposed or upper surfaces of die 12 having a planar surface area of between approximately 0.25-0.50 mm square or larger and a thickness of approximately 25-50 microns or greater can collectively exhibit a vertical deviation from the wafer or film frame processing plane 192 of less than approximately +/−100 µm, or less than approximately 10 to 90 µm (e.g., less than approximately +/−20 to 80 µm, or on average less than approximately 50 µm). Very small or ultra-small die 12 (e.g., approximately 0.25-0.55 mm square) and/or very thin or ultra-thin die 12 (e.g., approximately 25-75 µm or approximately 50 µm thick) can be maintained within an inspection plane 192 such that their deviation out of the inspection plane 192 is less than approximately 20-50 µm.

As previously indicated, the maximum transverse dimension or diameter of a given volume 140 of porous material within a particular base tray compartment 130, as well as the planar spatial extent or surface area spanned by a ridge 120 that defines or limits the maximum planar spatial extent or surface area of the compartment 130 in which the volume 140 of porous material resides, is correlated with or corresponds to a particular standard or expected wafer and/or film frame size, planar spatial extent or surface area, dimension, or diameter. More particularly, in order to securely hold or retain a wafer 10 or film frame 30 of a given size to the wafer table planar surface 190, vacuum force is provided or delivered to the wafer 10 or film frame 30 by way of selectively providing or delivering vacuum force to or through the vacuum opening(s) 20 disposed within or exposed to the compartment 130 having a maximum transverse dimension or diameter that most closely matches the transverse dimension or diameter of the wafer or film frame size currently under consideration, as well as each compartment 130 corresponding to a wafer or film frame size that is smaller than that of the wafer 10 or film frame 30 currently under consideration. Thus, a wafer 10 or film frame 30 of a particular size should entirely cover the upper surface of (a) a volume 140 of porous material having a transverse dimension or diameter that most closely matches the size of the wafer 10 or film frame 30 under consideration, as well as (b) each volume 140 of porous ceramic material having a smaller transverse dimension or diameter. A wafer 10 or film frame 30 should also cover a portion of the ridge 120 that most closely matches the size of the wafer 10 or film frame 30, as well as each ridge 120 having a diameter that is smaller than the wafer 10 or film frame 30 under consideration.

Figure 3E:
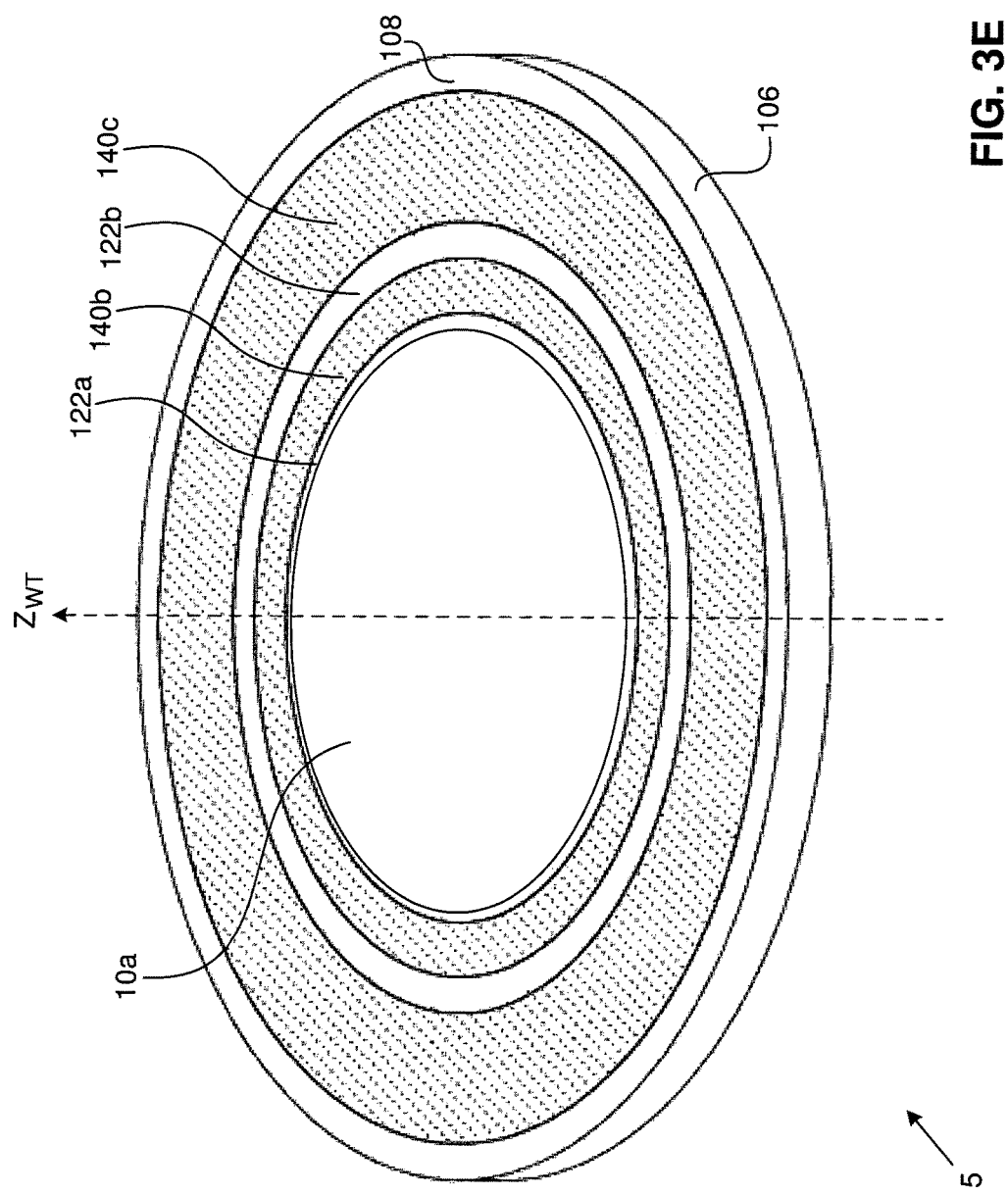
FIG. 3E is a perspective view of a representative first wafer having a first standard diameter (e.g., 8 inches) disposed upon a vacuum chuck structure in accordance with an embodiment of the present disclosure.

FIG. 3E is a perspective view of a representative first wafer 10a having a first standard diameter (e.g., 8 inches) disposed upon a wafer table structure 5 in accordance with an embodiment of the present disclosure, such that the first wafer 10a can be securely retained upon the wafer table planar surface 190 by way of (a) the first wafer 10a covering the first volume 140a of porous material and covering at least a portion of the transverse width of the first ridge 120a, but not extending to or overlapping with the second volume 140b of porous material; and (b) the application or delivery of vacuum force to the first wafer 10a by way of selective or preferential provision of vacuum force to or through the first compartment's vacuum opening 20, into and through the first volume 140a of porous material, to an underside of the first wafer 10a.

Figure 3F:
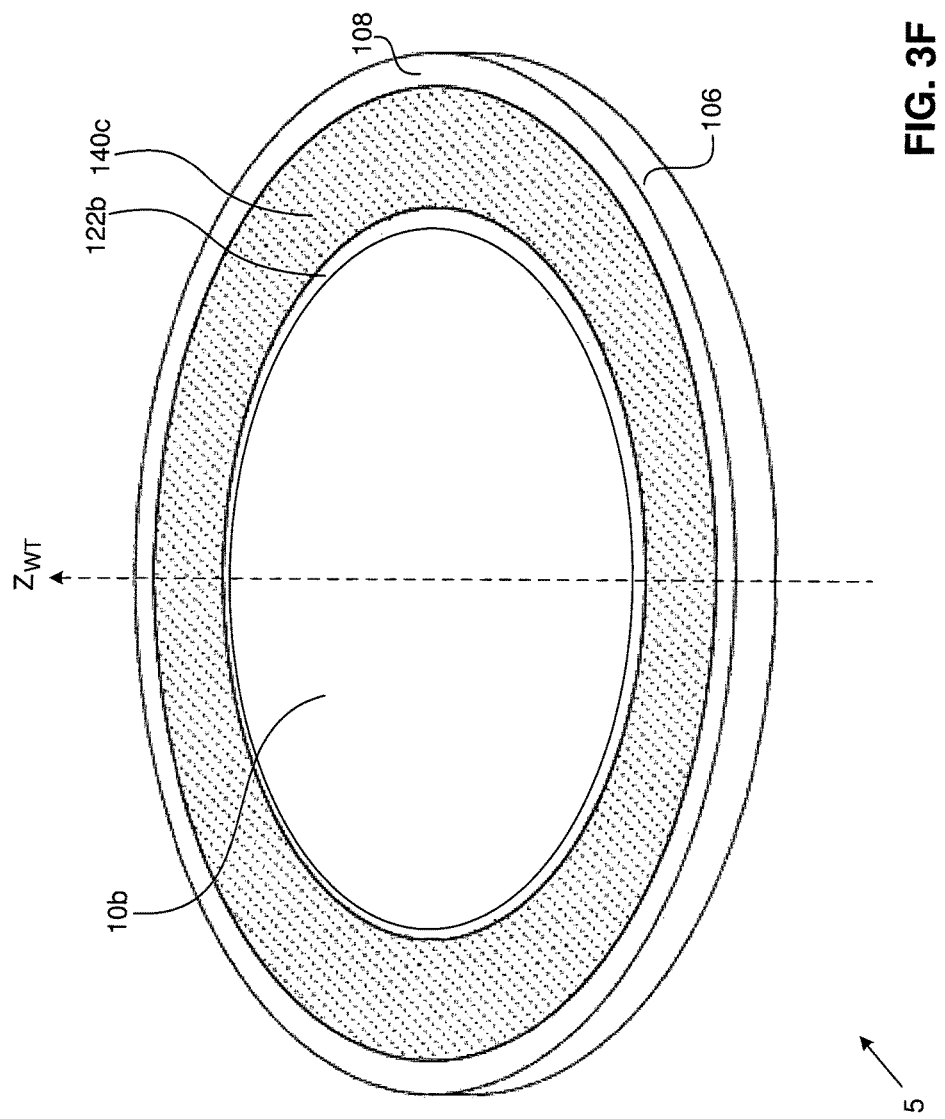
FIG. 3F is a perspective view of a representative second wafer having a second standard diameter (e.g., 12 inches) disposed upon a vacuum chuck structure in accordance with an embodiment of the present disclosure.

FIG. 3F is a perspective view of a representative second wafer 10b having a second standard diameter (e.g., 12 inches) disposed upon a wafer table structure 5 in accordance with an embodiment of the present disclosure. The second wafer 10b can be securely retained upon the wafer table planar surface 190 by way of (a) the second wafer 10b covering the first and second volumes 140a-b of porous material and covering at least a portion of the transverse width of the second ridge 120b, but not extending to or overlapping with the third volume 140c of porous material; and (b) the application or delivery of vacuum force to the second wafer 10b by way of selective or preferential provision of vacuum force to or through the first compartment's vacuum opening 20 and the second compartment's vacuum openings 20, into and through the first and second volumes 140a-b of porous material, to an underside of the second wafer 10b.

Figure 3G:
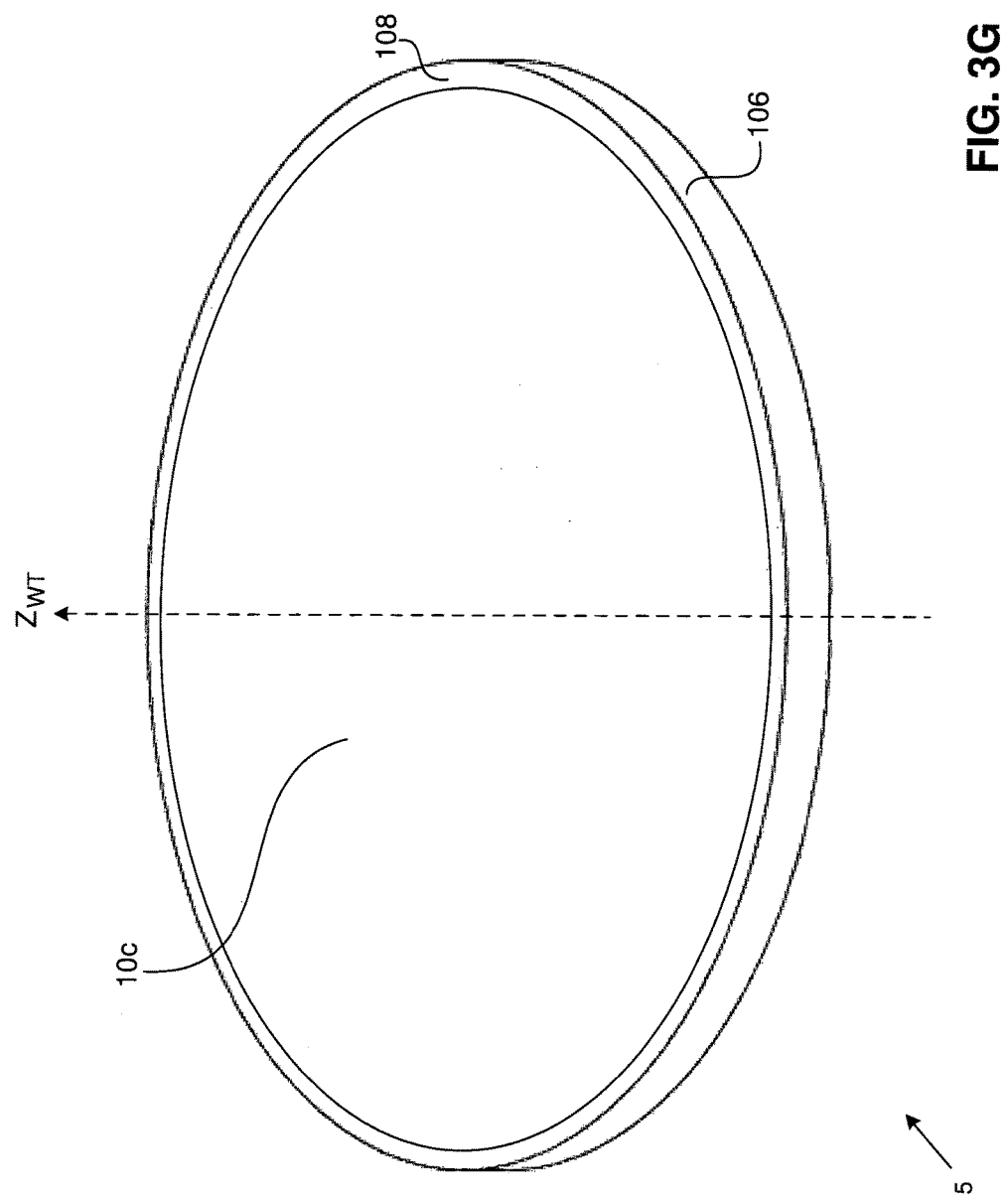
FIG. 3G is a perspective view of a representative third wafer having a third standard diameter (e.g., 16 inches) disposed upon a vacuum chuck structure in accordance with an embodiment of the present disclosure.

FIG. 3G is a perspective view of a representative third wafer 10c having a third standard diameter (e.g., 16 inches) disposed upon a wafer table structure 5 in accordance with an embodiment of the present disclosure. The third wafer 10c can be securely retained upon the wafer table planar surface 190 by way of (a) the third wafer 10c covering the first, second, and third volumes 140a-c of porous material and covering a portion of the transverse width of the base tray's outer border 106; and (b) the application or delivery of vacuum force to the third wafer 10c by way of selective or preferential provision of vacuum force to or through the first compartment's vacuum opening 20, the second compartment's vacuum openings 20, and the third compartment's vacuum openings 20, into and through the first, second, and third volumes 140a-c of porous material, to an underside of the third wafer 10c.

In addition to the foregoing, in a number of embodiments a ceramic based base tray 100 can include or be formed to accommodate or provide one or more additional types of structural features or elements. Particular representative non-limiting embodiments of such ceramic based trays 102 are described in detail hereafter.

FIG. 4A is a perspective view of a ceramic based wafer table base tray 100 in accordance with another embodiment of the present disclosure, which includes a set of ejector pin guide members 160. FIG. 4B is a cross-sectional view of the ceramic based wafer table base tray of FIG. 4A, taken thorough a line C-C'. In such an embodiment, the base tray 100 can have a general or overall structure that is analogous or substantially identical to that described above. However, the first ridge 110a includes a number of ejector pin guide structures, elements, or members 160a-c (e.g., three in various embodiments, which is sufficient for enabling three ejector pins to handle each of 8 inch, 12 inch, and 16 inch wafers corresponding to such wafer sizes). Each ejector pin guide member 106a-c is shaped and configured for providing an opening 162 corresponding to or defining a passage or pathway through which an ejector pin can travel. In multiple embodiments, any given ejector pin guide member 160a-c can be formed as an integral portion or extension of the first ridge 110a, such that the ejector pin guide member 160a-c protrudes into a portion of the first compartment 120a. Moreover, ejector pin guide members 160a-c are dimensioned and/or constructed in such a manner such that essentially no, negligible, or minimal vacuum loss occurs through the ejector pin guide members 160a-c during wafer table structure use (e.g., during ejector pin elevation and lowering). In several embodiments, ejector pin guide members 160a-c can be strategically disposed such that a single set of ejector pins 164 can handle each wafer size that the wafer table structure 5 is designed to handle. One of ordinary skill in the relevant art will understand that ejector pin guide members 160a-c could alternatively or additionally be formed separate from the first ridge 110a, or as a portion of another ridge 110 (e.g., the second ridge 110b).

Figure 5A:
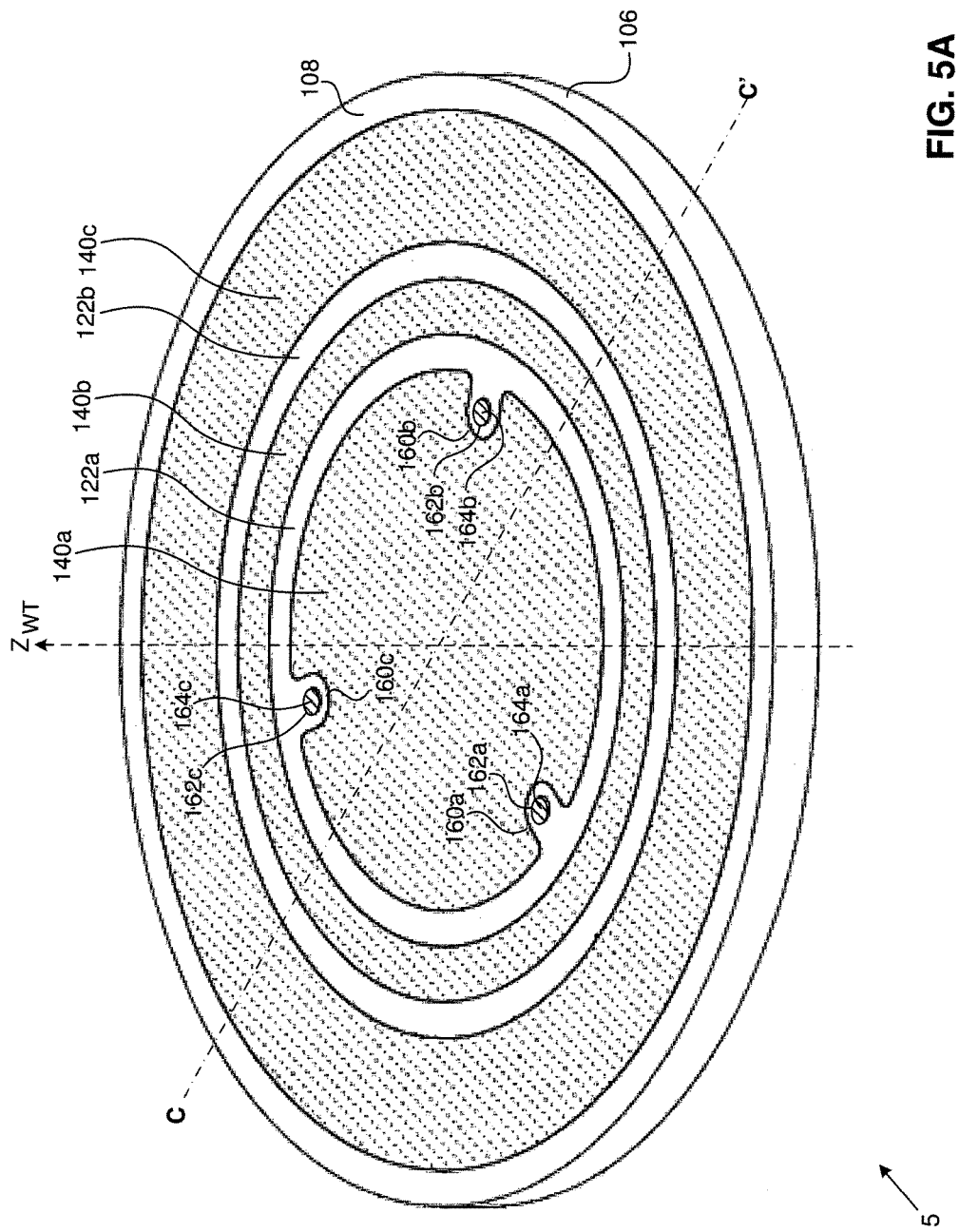
FIG. 5A is a perspective view of the base tray of FIGS. 2A and 2B, into which a moldable, formable, conformable, or flowable porous ceramic based material has been disposed.
Figure 5B:
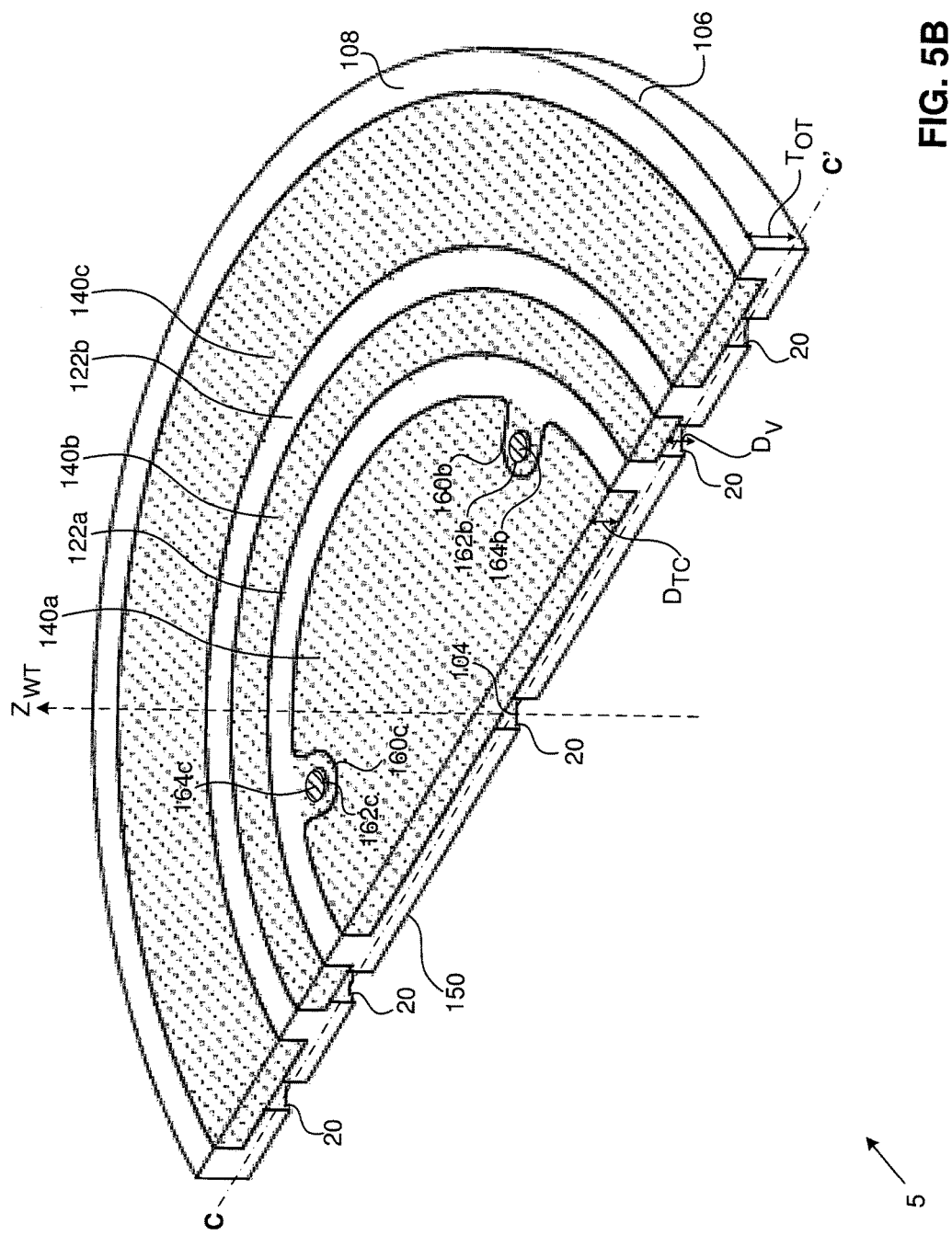
FIG. 5B is a perspective cross sectional view of the base tray carrying the moldable, formable, or flowable porous ceramic based material corresponding to FIG. 5A, taken through a line D-D'.

FIG. 5A is a perspective view of the base tray 100 of FIGS. 4A and 4B into which a moldable, formable, conformable, or flowable porous material has been introduced, provided, or disposed. FIG. 5B is a perspective cross sectional view of the base tray 100 carrying the moldable porous material corresponding to FIG. 5A, taken through a line D-D'. It should be noted that when the moldable porous material is introduced into the base tray 100, the opening 162 within and through each ejector pin guide member 160a-c should be sealed or blocked, such that porous material is excluded from the opening 162 and the passage through the ejector pin guide member 160a-c corresponding thereto in order to ensure that travel of an ejector pin 164a-c through the passage and the opening 162 is not impeded by hardened moldable porous material during ejector pin actuation involving the lowering or raising of wafers or film frames relative to the wafer table planar surface 190.

In some embodiments, the base tray 100 can carry, include, or incorporate a number of heating and/or cooling elements. For instance, heating elements can include resistive heating elements. Cooling elements can include tubes, channels, or passages which are configured for carrying a cooling substance or fluid (e.g., a chilled gas, or a liquid); or a thermoelectric cooling device. Heating and/or cooling elements can be enclosed or encapsulated within the non-porous ceramic based base tray material (e.g., integrally formed within one or more portions of the base tray 100). Alternatively, heating and/or cooling elements can reside external to the non-porous ceramic based base tray material, enclosed or encapsulated within portions of the porous material that occupies the base tray receptacles 130. In addition or as an alternative to the foregoing, the non-porous ceramic based base tray 100 and/or the porous material that occupies the base tray receptacles 130 can carry, include, or incorporate additional or other types of elements, such as electrodes, temperature sensing elements (e.g., thermocouples), other types of sensing elements (e.g., accelerometers, vibration sensors, or optical sensors), and/or other types of sensing elements configured for sensing surrounding/environmental conditions within and/or external to portions of the wafer table structure 5.

Figure 6:
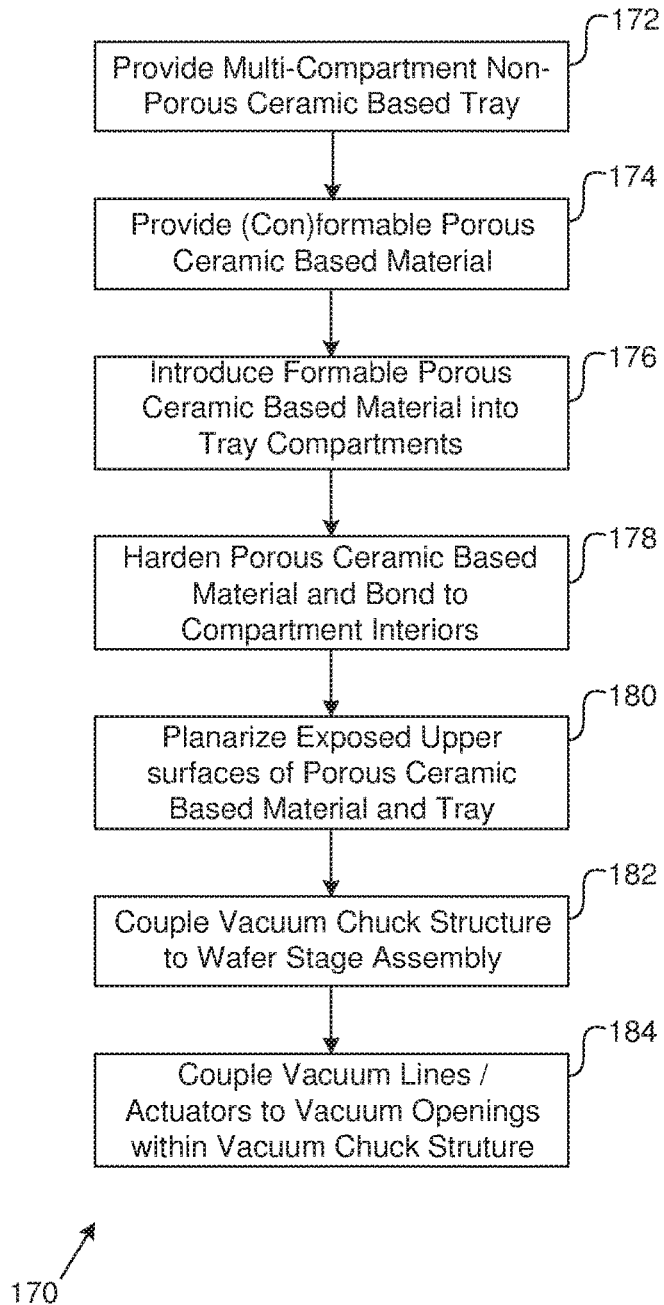
FIG. 6 is a flow diagram of a representative process for manufacturing a vacuum chuck structure in accordance with an embodiment of the present disclosure.
Figure 7:
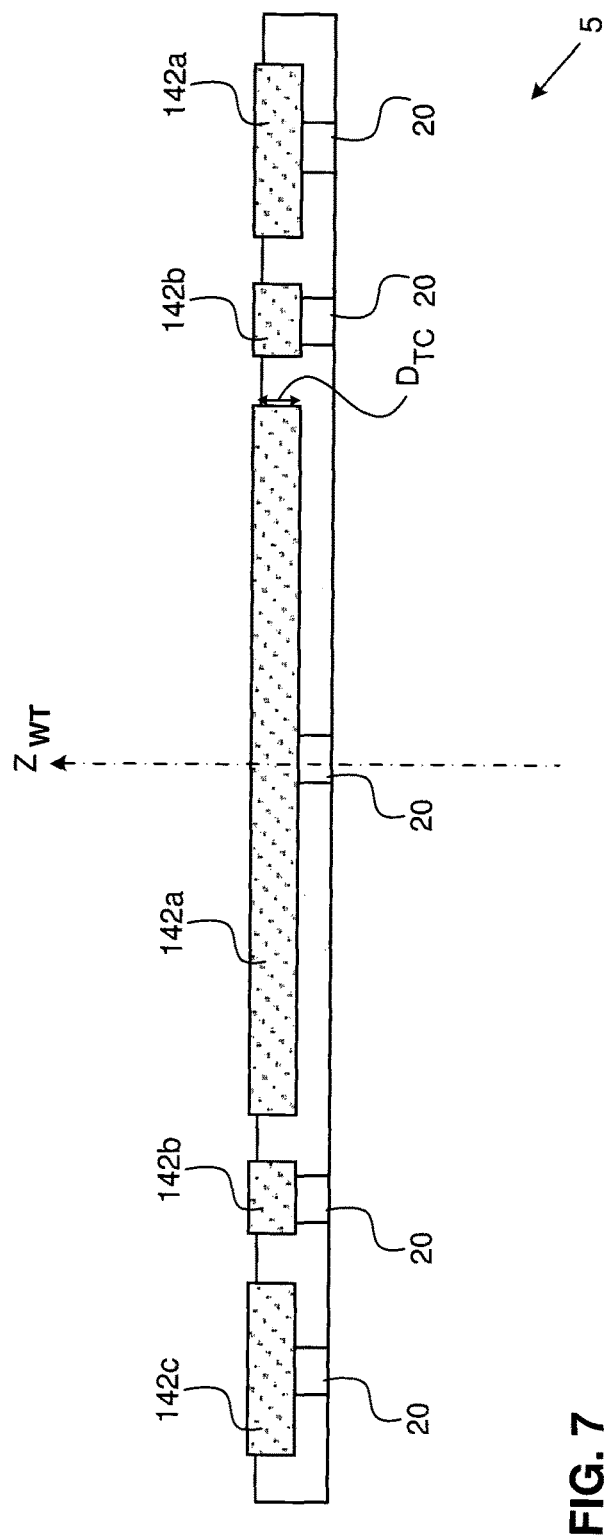
FIG. 7 is a cross sectional view of a vacuum chuck structure in accordance with an embodiment of the present disclosure, which illustrates initial volumes of moldable porous ceramic based material slightly exceeding base tray compartment volumes before completion of a planarization process.

FIG. 6 is a flow diagram of a representative process 170 for manufacturing a wafer table structure 5 in accordance with an embodiment of the present disclosure. In an embodiment, a wafer table manufacturing process 170 includes a first process portion 172 involving providing a non-porous ceramic based wafer table base tray 100 having a plurality of compartments 130 therein; a second process portion 174 involving providing a moldable porous material; and a third process portion 176 comprising introducing the moldable porous material into the plurality of compartments 130 and filling the volumetric geometry of each compartment 130 within the plurality of compartments 130 with the moldable porous material, such that the moldable porous material conforms to or occupies the inner spatial dimensions of each compartment 130. Within each compartment 130, an initial volume 142 of moldable porous ceramic material can exceed or slightly exceed the volumetric capacity of the compartment 130 by way of the moldable porous ceramic material exhibiting a depth or thickness that exceeds the depth $D_{TC}$ of a base tray compartment 130, for instance, in a manner indicated or generally indicated in FIG. 7.

A fourth process portion 178 involves hardening or curing the moldable porous ceramic material and bonding the porous material to the inner surfaces (i.e., inner bottom surfaces 110 within the base tray 100 and compartment sidewalls corresponding to ridges 120) defining each compartment 130. Once the porous material is securely retained within or bonded to compartment inner surfaces, a fifth process portion 180 involves machining or polishing the porous material (i.e., each porous material volume 140) as well as portions of the base tray 110 such as exposed upper surfaces 122 of base tray ridges 120 and an exposed upper surface 108 of the base tray outer border 106 in order to simultaneously provide exposed, upper, or outer surfaces of porous material volumes 140, exposed upper surfaces 122 of base tray ridges 120, and the exposed upper surface 108 of the base tray outer border 106 with a very high degree of planarity, thereby defining a highly uniform wafer table planar surface 190 upon which wafers and film frames can be securely retained. Once planarized, each porous material volume 140 corresponding to any given compartment 130 is identical or essentially identical to the volume of the compartment 130.

A sixth process portion 182 involves coupling or mounting the planarized wafer table structure 5 to a displaceable wafer table or stage assembly (e.g., an x-y wafer stage), and coupling vacuum openings 20 within the planarized wafer table structure 5 to a set of stage assembly vacuum lines, links, and/or valves, such that vacuum force can be selectively actuated and applied to wafers 10 or film frames 30 disposed upon the wafer table planar surface 190.

In contrast to certain prior wafer table designs in which regions of porous material are separated by partitions made or substantially made of one or more metals, and/or which utilize an outer receptacle structure made or substantially made of one or more metals, various embodiments of wafer table structures in accordance with the present disclosure avoid or exclude ridges 120 made or substantially made of one or more metals, and typically further avoid or exclude a base tray 100 that is made or substantially made of one or more metals. More particularly, in prior wafer table designs that include upper or exposed non-porous wafer table surfaces that are at least partially or substantially made of metal, as well as upper or exposed porous wafer table surfaces that are at least substantially made of a ceramic material, such metal surfaces have quite different machining, grinding, or polishing characteristics, properties, or behavior than the porous ceramic material surfaces. During a machining, grinding, or polishing process, the metal surfaces will not planarize at the same rate or as readily as the porous ceramic material surfaces. Moreover, the metal surfaces can readily damage standard machining, grinding, or polishing elements, devices, or tools (e.g., polishing heads). The inclusion of metal surfaces makes the machining, grinding, or polishing process significantly more difficult, expensive, and time consuming compared to wafer table structures manufactured in accordance with embodiments of the present disclosure.

Furthermore, the difference between the machining, grinding, or polishing characteristics of the exposed metal surfaces and the exposed porous ceramic surfaces significantly increases the likelihood that the final as-manufactured wafer table surface will exhibit undesirable or unacceptable non-planarity, or insufficient planarity, across one or more sections or regions of the wafer table surface. Such prior wafer table designs are therefore not well suited for the inspection of large diameter, thin wafers 10 having fragile die 12 thereon, such as 12-inch or larger sawn wafers 10 carried by film frames 30 which carry small or ultra-small die 12. In contrast, wafer table structure embodiments in accordance with the present disclosure do not suffer from this drawback, and provide a highly uniform or ultra-uniform planar wafer table surface 622 that is very well suited to the inspection of such types of wafers 10 or film frames 30.

The end result of a wafer table structure manufactured in accordance with embodiments of the present disclosure is a wafer table 620 that (a) excludes or omits grooves or vacuum holes (e.g., drilled vacuum holes) on the wafer table surface 622 that can adversely affect the planarity of the wafer table surface 622 and result in one or more of the associated problems previously described; (b) has a very high or ultra-high planarity wafer table surface 622 suitable for handling (i) both wafers 10 and film frames 30, thereby eliminating the need for wafer table conversion kits, and (ii) very small or ultra-small die 12 (e.g., 0.5 mm×0.5 mm square, or smaller) residing on very thin or flexible wafers (e.g., 75 µm, 50 µm, or thinner), as the planar wafer table surface 622 facilitates the positioning and maintenance of such die 12 in/on a single plane, which may be difficult to achieve using conventional wafer table designs; and (c) structurally straightforward, low cost, and easy to manufacture, particularly compared to conventional wafer table designs which include grooves or machined/drilled vacuum holes on their wafer table surface, and/or exposed metal materials on their wafer table surface (e.g., metal plates, or a number of metal partitions across the wafer table surface).

Aspects of various embodiments in accordance the present disclosure address at least one aspect, problem, limitation, and/or disadvantage associated with existing systems and methods for handling wafers and/or film frames, including one or more problems, limitations, and/or disadvantages associated with existing wafer table structures. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. A wafer table structure providing a wafer table surface suitable for handling wafers, portions of wafers, and film frames on which wafers or portions thereof are mounted, the wafer table structure comprising:
   a base tray comprising a first set of exposed upper surfaces, an interior surface, and a set of compartments formed integrally with or attached to the interior surface, the base tray formed of at least one type of material that is gas or fluid impermeable in response to applied negative pressures;
   at least one type of compartment material disposed within the set of compartments, the at least one type of compartment material conformable to the set of compartments and hardenable to provide a hardened compartment material in the set of compartments that is gas or fluid permeable in response to applied vacuum forces, and which provides a second set of exposed upper surfaces; and
   a set of openings formed in the interior surface of the base tray, by which the hardened compartment material is exposable to negative pressures or positive pressures,
   wherein (a) the first set of exposed upper surfaces of the base tray and (b) the second set of exposed upper surfaces of the hardened compartment material are simultaneously machinable by way of a common machining process to provide a planar wafer table surface for carrying wafers and film frames,
   wherein the set of compartments comprises a plurality of compartments, the wafer table structure further comprises a set of ridges that separates individual compartments within the plurality of compartments from each other, and the first set of exposed upper surfaces of the base tray includes exposed upper surfaces of the set of ridges,
   wherein the interior surface of the base tray includes a plurality of inner bottom surfaces, each ridge within the set of ridges borders an inner bottom surface of the base tray, and each ridge within the set of ridges partitions portions of different base tray inner bottom surfaces from each other to define the set of compartments,
   wherein each ridge within the set of ridges resides at a predetermined distance away from a center of the base tray, and wherein at least a first compartment is surrounded by a ridge,
   wherein the base tray and each ridge within the set of ridges are formed from identical materials,
   wherein each ridge within the set of ridges and each compartment within the set of compartments is dimensioned in a manner correlated with a standard wafer size or a standard film frame size, and
   wherein
   (a) the set of compartments includes:
      a first compartment containing a first volume of hardened compartment material exposed to a first set of openings corresponding thereto; and
      a second compartment containing a second volume of compartment material exposed to a second set of openings corresponding thereto, the second set of openings distinct from the first set of openings, and
   (b) a first ridge within the set of ridges surrounds the first compartment to thereby separate the first compartment from the second compartment.

2. The wafer table structure of claim 1, wherein the planar wafer table surface excludes grooves and vacuum holes formed therein.

3. The wafer table structure of claim 2, wherein the planar wafer table surface is a planar surface that facilitates positioning and maintaining wafer die in or on a single plane, and wherein the planar wafer table surface has a planar uniformity across the planar wafer table surface of less than +/−100 pm.

4. The wafer table structure of claim 1, wherein a rate at which the first set of exposed upper surfaces of the base tray is planarized by the common machining process and a rate at which the second set of exposed upper surfaces of the hardened compartment material is planarized by the common machining process are essentially identical.

5. The wafer table structure of claim 1, wherein negative pressure is to be applied to the first set of openings to securely retain a first wafer or first film frame having a first standard diameter to the planar wafer table surface, and wherein negative pressure is to be applied to the first set of openings and the second set of openings to securely retain a second wafer or second film frame having a second standard diameter larger than the first standard diameter to the planar wafer table surface.

6. The wafer table structure of claim 5, wherein:
   (c) the set of compartments includes a third compartment containing a third volume of hardened compartment material exposed to a third set of openings corresponding thereto, the third set of openings distinct from each of the first set of openings and the second set of openings; and (d) a second ridge within the set of ridges surrounds the second compartment to thereby separate the second compartment from the third compartment.

7. The wafer table structure of claim 6, wherein negative pressure is to be applied to the first set of openings, the second set of openings, and the third set of openings to securely retain a third wafer or a third film frame having a third standard diameter larger than each of the first and second standard diameters to the planar wafer table surface.

8. The wafer table structure according to claim 1, wherein at least one of the base tray and the hardened compartment material comprises a ceramic based material.

9. The wafer table structure of claim 8, wherein the base tray comprises porcelain.

10. The wafer table structure of claim 1, further comprising a single set of ejector pin guide members through which a single set of ejector pins is configured to travel for handling wafers of multiple standard sizes.

11. A method for manufacturing a wafer table structure providing a wafer table surface suitable for handling wafers, portions of wafers, and/or and film frames on which wafers or portions thereof are mounted, the method comprising: providing a base tray having a first set of exposed upper surfaces, an interior surface, a set of compartments formed integrally with or attached to the interior surface, and at least one set of openings formed in the interior surface, the base tray formed of at least one type of material that is gas or fluid impermeable in response to applied negative pressures; disposing at least one type of compartment material within the set of base tray compartments, the at least one type of compartment material conformable to the set of compartments; hardening the at least one type of compartment material to provide a hardened compartment material in the set of compartments that is gas or fluid permeable in response to applied negative pressures or positive pressures, and which provides a second set of exposed upper surfaces; and simultaneously machining the first set of exposed upper surfaces and the second set of exposed upper surfaces by way of a common machining process to provide a planar wafer table surface for carrying wafers and film frames on which wafers or portions thereof are mounted; wherein the set of compartments comprises a plurality of compartments, wherein the wafer table structure further comprises a set of ridges that separates individual compartments within the plurality of compartments from one another, and
- a single set of ejector pin guide members through which a single set of ejector pins is configured to travel for handling wafers of multiple standard sizes,
- wherein the first set of exposed upper surfaces of the base tray includes exposed upper surfaces of the set of ridges, wherein the interior surface of the base tray includes a plurality of inner bottom surfaces, each ridge within the set of ridges borders an inner bottom surface of the base tray, and each ridge within the set of ridges partitions portions of different base tray inner bottom surfaces from one another to define the set of compartments, wherein each ridge within the set of ridges resides at a predetermined distance away from a center of the base tray, wherein each ridge within the set of ridges and each compartment within the set of compartments is dimensioned in a manner correlated with a standard wafer size or a standard film frame size, and wherein (a) the set of compartments includes: a first compartment containing a first volume of hardened compartment material exposed to a first set of openings corresponding thereto: and second compartment containing a second volume of compartment material exposed to a second set of openings corresponding thereto, the second set of openings distinct from the first set of openings, and
- (b) a first ridge within the set of ridges surrounds the first compartment to thereby separate the first compartment from the second compartment.

12. The method of claim 11, wherein during the simultaneous machining of the first and second sets of exposed upper surfaces, a rate at which the first set of exposed upper surfaces of the base tray is planarized by the common machining process and a rate at which the second set of exposed upper surfaces of the hardened compartment material is planarized by the common machining process are essentially identical.

13. The method of claim 11, wherein at least one of the base tray and the hardened compartment material comprises a ceramic based material.

14. The method of claim 11, further comprising: mounting the wafer table structure to a displaceable wafer table or stage assembly; and coupling each set of openings to a set of lines through which negative pressure or positive pressure is can be selectively actuated and applied to wafers or film frames disposed upon the planar wafer table surface.

15. The method of claim 11, wherein the base tray and each ridge within the set of ridges are formed from identical materials.

16. A wafer table structure providing a wafer table surface suitable for handling wafers, portions of wafers, and film frames on which wafers or portions thereof are mounted, the wafer table structure comprising:
- a base tray comprising a first set of exposed upper surfaces, an interior surface, and a set of compartments formed integrally with or attached to the interior surface, the base tray formed of at least one type of material that is gas or fluid impermeable in response to applied negative pressures;
- at least one type of compartment material disposed within the set of compartments, the at least one type of compartment material conformable to the set of compartments and hardenable to provide a hardened compartment material in the set of compartments that is gas or fluid permeable in response to applied vacuum forces, and which provides a second set of exposed upper surfaces;
- a set of openings formed in the interior surface of the base tray, by which the hardened compartment material is exposable to negative pressures or positive pressures; and
- a single set of ejector pin guide members through which a single set of ejector pins is configured to travel for handling wafers of multiple standard sizes,
- wherein (a) the first set of exposed upper surfaces of the base tray and (b) the second set of exposed upper surfaces of the hardened compartment material are simultaneously machinable by way of a common machining process to provide a planar wafer table surface for carrying wafers and film frames,
- wherein the set of compartments comprises a plurality of compartments, the wafer table structure further comprises a set of ridges that separates individual compartments within the plurality of compartments from each other, and the first set of exposed upper surfaces of the base tray includes exposed upper surfaces of the set of ridges,
- wherein the interior surface of the base tray includes a plurality of inner bottom surfaces, each ridge within the set of ridges borders an inner bottom surface of the base tray, and each ridge within the set of ridges partitions portions of different base tray inner bottom surfaces from each other to define the set of compartments, wherein each ridge within the set of ridges resides at a predetermined distance away from a center of the base tray, and wherein at least a first compartment is surrounded by a ridge, wherein each ridge within the set of ridges and each compartment within the set of compartments is dimensioned in a manner correlated with a standard wafer size or a standard film frame size, and wherein (a) the set of compartments includes:
- a first compartment containing a first volume of hardened compartment material exposed to a first set of openings corresponding thereto; and
- a second compartment containing a second volume of compartment material exposed to a second set of openings corresponding thereto, the second set of openings distinct from the first set of openings, and (b) a first ridge within the set of ridges surrounds the first compartment to thereby separate the first compartment from the second compartment.

* * * * *